United States Patent
Dube et al.

(10) Patent No.: US 6,269,144 B1
(45) Date of Patent: Jul. 31, 2001

(54) METHOD AND APPARATUS FOR DIFFRACTION MEASUREMENT USING A SCANNING X-RAY SOURCE

(76) Inventors: William P. Dube, 2035 Dahlia St., Denver, CO (US) 80207; Richard Albert, 317 Hartford Rd., Danville, CA (US) 94526; Thomas A. Siewert, 2380 Kohler Dr., Boulder, CO (US) 80303; Dale W. Fitting, 2785 Heather Rd., Golden, CO (US) 80401

(*) Notice: Subject to any disclaimer, the term of this patent is extended or adjusted under 35 U.S.C. 154(b) by 0 days.

(21) Appl. No.: 09/034,918

(22) Filed: Mar. 4, 1998

(51) Int. Cl.⁷ .................................................. G01N 23/20
(52) U.S. Cl. .................................................. 378/71
(58) Field of Search ........................... 378/71–81, 98.6, 378/137

(56) References Cited

U.S. PATENT DOCUMENTS

| | | | |
|---|---|---|---|
| 2,837,657 | 6/1958 | Craig et al. | 250/65 |
| 3,373,286 | 3/1968 | Han | 250/105 |
| 3,702,933 | 11/1972 | Fields et al. | 250/51.5 |
| 3,833,810 | * 9/1974 | Efanow et al. | 378/98.6 |
| 3,885,153 | 5/1975 | Schoenborn et al. | 250/251 |
| 3,904,876 | 9/1975 | Arendt | 250/273 |
| 3,980,568 | 9/1976 | Pitchford et al. | 250/276 |
| 4,065,211 | 12/1977 | Vig | 356/152 |
| 4,104,519 | 8/1978 | Oldendorf | 250/274 |
| 4,147,935 | 4/1979 | Warrikhoff | 250/416 |
| 4,274,000 | 6/1981 | Goebel | 250/272 |
| 4,467,199 | 8/1984 | Sato | 250/310 |
| 4,922,442 | 5/1990 | Bolk et al. | 364/550 |
| 4,928,294 | 5/1990 | Beard, Jr. et al. | 378/74 |
| 5,008,910 | 4/1991 | Van Egeraat | 378/84 |
| 5,195,115 | 3/1993 | Schiller et al. | 378/73 |
| 5,204,888 | 4/1993 | Tamegai et al. | 378/53 |
| 5,263,075 | 11/1993 | McGann et al. | 378/147 |
| 5,274,435 | 12/1993 | Hettrick | 356/328 |
| 5,384,817 | 1/1995 | Crowther et al. | 378/84 |
| 5,406,609 | 4/1995 | Arai et al. | 378/73 |
| 5,446,777 | 8/1995 | Houtman | 378/45 |
| 5,457,727 | 10/1995 | Frijlink | 378/73 |
| 5,481,109 | 1/1996 | Ninomiya et al. | 250/310 |
| 5,497,008 | 3/1996 | Kumakhov | 250/505.1 |
| 5,521,999 | 5/1996 | Chuang et al. | 385/88 |
| 5,684,857 | 11/1997 | De Bokx | 378/45 |
| 5,692,029 | 11/1997 | Husseiny et al. | 378/88 |

* cited by examiner

*Primary Examiner*—Craig E. Church
(74) *Attorney, Agent, or Firm*—Theodore J. Bielen, Jr.

(57) ABSTRACT

The present invention relates to x-ray diffraction measurement by using moving x-ray source x-ray diffraction. The invention comprises a raster-scanned x-ray source, a specimen, a collimator, and a detector. The x-ray source is electronically scanned which allows a complete image of the x-ray diffraction characteristics of the specimen to be produced. The specimen is placed remote from the x-ray source and the detector. The collimator is located directly in front of the detector. The x-rays are diffracted by the specimen at certain angles, which cause them to travel through the collimator and to the detector. The detector may be placed in any radial location relative to the specimen in order to take the necessary measurements. The detector can detect the intensity and/or the wavelength of the diffracted x-rays. All information needed to solve the Bragg equation as well as the Laue equations is available. The x-ray source may be scanned electronically or mechanically. The present invention is used to perform texture analysis and phase identification.

48 Claims, 13 Drawing Sheets

```
Start
Input d, Jsize, Ksize, X - 601
For J = 0 to Jsize - 602
For K = 0 to Ksize - 603
`move radiation source RasterTo(J,K) - 604
`calculate distance R between source location and centroid of sensed volume
Xr,Yr,Zr = SourceLocation(J,K) - 605
Xc,Yc,Zc = SVLocation(L) - 606
R = Sqrt((Xr-XC)²+(Yr-Yc)²+(Zr-Zc)²) - 607
calculate angle 2θ between path along distance R and collimator path
2θ = ArcCos((Zr-Zc)/R) - 608
`calculate rotation angle γ about collimator path
γ=ArcCos((Xr-Xc)/(R*Sin(2θ))) - 609
`calculate needed λ  λ = 2*d*sin(θ) - 610
`set SCA programming signal to λ SetSCA(λ) - 611
`reset SCA counter Counter - 0 - 612
Wait X milliseconds for photon counts to accumulate - 613
`read SCA counter Counts = Counter - 614
`correct intesity for distance BetterCounts = R² * Counts - 615
`correct intesity for spectral variation of source
EvenBetterCounts - BetterCounts/SourceIntensity(λ) - 616
`plot point on unit radius sphere in reciprocal space
Recip(2θ,γ) =EvenBetterCounts - 617
`plot symmetric points on orientation distribution function
ODF(θ,γ) =EvenBetterCounts - 618
ODF((θ+180),γ) = EvenBetterCounts - 619
Next K - 620
Next J - 621
End
```

Fig. 6

```
Start
Input Jsize,Ksize, X, Max_d - 701 User sets
λ of SCA - 702 For I - 0 to Max_d - 703
dTrace(I) = 0 - 704 dTraceCounter(I) - 0 -
705 Next I - 706 For J = 0 to Jsize - 707
For K - 0 to Ksize - 708 `move radiation
source RasterTo(J,K) - 709 `calculate
distance along path R between radiation
source and centroid of sensed volume
Xr,Yr,Zr = SourceLocation(J,K) - 710
Xc,Yc,Zc = SVLocation(L) - 711 R = Sqrt((Xr-
Xc)² + (Yr-Yc)² + (Zr-Zc)²) - 712 `calculate
angle 2θ between path along distance R and
collimator path 2θ = ArcCos((Zr-Zc)/R) - 713
`reset counter Counter - 0 - 714 Wait X
milliseconds for photon counts to accumulate
- 715 `read counter Counts = Counter -716
`calculate "d" spacing using Bragg equation
d = λ/(2*Sin(θ)) - 717 `correct intensity
for distance BetterCounts = R² + Counts -
718 `sum point into intensity vs "d" trace
dTrace(d) += BetterCounts - 719 `increment
corresponding counter dTraceCounter(d) += 1
- 720
Next K - 721
Next J - 722
For I - 0 to Max_d - 722
DTrace(I) /= dTraceCounter(I) - 723
Next I - 724
End
```

Fig. 7

```
Start
Input Jsize,Ksize,Max_d,X - 801
For I = to Max_d - 802
dTrace(I) = 0 - 803
dTraceCounter(I) = 0 - 804
Next I - 805
For J = 0 to Jsize - 806
For K = 0 to Ksize - 807 `move source
RasterTo(J,K) - 808 `calculate distance R between
source location and centroid of sensed volume
Xr,Yr,Zr = SourceLocation(J,K) - 809 Xc,Yc,Zc =
SVLocation(L) - 810 R - Sqrt((Xr-Xc)² + (Yr-Yc)² +
(Zr-Zc)²) - 811 `calculate angle 2θ between path
along distance R and collimator path 2θ =
ArcCos((Zr-Zc)/R) - 812 `reset MCA memory
ResetMCA() - 813 `start MCA StartMCA() - 814 Wait
X milliseconds for photon counts to accumulate -
815 `stop MCA StopMCA() - 816 For L = 0 to
NumberOfBins - 817 Counts - MCAbin(I) - 818
`calculate λ for particular bin λ =
MCAbinLambda(L) - 819 `correct for source spectrum
intensity variation BetterCounts =
Counts/SourceSpectrum(λ) - 820 `correct intensity
for distance EvenBetterCounts = R² * Bettercounts
- 821 `calculate "d" spacing d - λ/(2*Sin(0)) -
822 sum in data to intensity vs "d" spacing trace
dTrace(d) += EvenBetterCounts - 823 `increment
corresponding counter dTraceCounter(d) +=1 - 824
Next L - 825
Next K -826
Next J - 827
For I = 0 to Max_d - 828
DTrace(I) /= dTraceCounter(I) - 829
Next I - 830
End
```

Fig. 8

```
Start
Input Isize,Jsize,Ksize,X - 902 Input
NumberOfSegments - 903 `acquire XRD data For I = 0
to Isize - 904 For J - 0 to Jsize - 905 For K = 0
Ksize - 906 Move Source to SourceLocation(I,J,K) -
907 Reset MCA memory - 908 Start MCA acquisition -
909 Wait X milliseconds for photon counts to
accumulate - 910 Stop MCA - 911 `store complete
MCA data PixelSpectrum(I,K,L) = MCAbinmemory - 912
Next K - 913 Next J - 914 Next I - 915 `extract
segment-specific XRD data For L = 0 to
NumberOfSegments - 916 `initialize Sspectrum and
Scount For n = 0 to θSize - 917 For m = 0 to γSize
- 918 Sspectrum(n,m) = nullSpectrum - 919
Scount(n,m) = 0 - 920 Next m - 921 Next n - 922
For I = 0 to Isize - 923  For J = 0 to Jsize - 924
For K = 0 Ksize - 925 `calculate path distance Rp
between source and segment controid Xs,Ys,Zs =
SourceLocation(I,J,K) - 926 Xc,Yc,Zc =
SegmentLocation(L) - 927 Rp = Sqrt((Xs-Xc)² + (Ys-
Yc)² + (Zs-Zc)²) - 928 `calculate angle 2θ between
path along distance Rp and collimator path 2θ =
ArcCos((Zs-Zc)/Rp) - 929 `calculate rotation angle
γ about collimator path γ = ArcCos((Xs-
Xc)/(Rp*Sin(2θ)) - 930 `correct intensity for
distance BetterPixelSpectrum = Rp² *
PixelSpectrum(I,J,K) - 931 Sspectrum(2θ,γ) =
BetterPixelSpectrum - 932 Scount(2θ,γ) =
Scount(2θ,γ) +1 - 933 Next K - 934 Next J - 935
Next I - 936 For n - 0 to θSize - 937 For m = 0 to
γSize - 938 Sspectrum(n,m)/= Scount(n,m) - 939
Next m - 940 Next n - 941 SegmentXRDpattern(L) =
Sspectrum - 942 Next L - 943 IF (Texture data
reduction) Then continue on Figure 10, step 1000 -
944 IF (Phase Identification) Then continue on
Figure 11, step 1100 - 945 END
```

Fig. 9

```
(Continued from figure 9, step 944) - 1000
`get desired "d" spacing
Input d - 1001
For L = 0 to NumberOfSegments - 1002
`select XRD data for segment L
Sspectrum = SegmentXRDpattern(L) - 1003
`initialize ODF and Recip
ODF = nullRecip - 1004
Recip = nullRecip - 1005
For 2θ - 0 to θSize - 1006
For γ = 0 to γSize - 1007
`retrieve a spectrum from element on "sphere" data
structure BinSet - Sspectrum(2θ,γ) - 1008
`calculate λ for "d" and 2θ λ = 2*d*Sin(θ) - 1009
n = MCAbinNumber(λ) - 1010
`get photon counts from bin Counts = BinSet(n) -
1011
`correct for radiation source spectrum variation
BetterCounts = Counts/SourceSpectrum(λ) - 1012
`transfer intensity data to Recip data structure
Recip(2θ,γ) - BetterCounts - 1013
`transfer intensity data to symmetric elements ODF
data structure ODF(θ,γ) = BetterCounts - 1014
ODF(θ + 180,γ) = BetterCounts - 1015
Next γ - 1016
Next 2θ - 1017
`store data in array of structures
RecipArray(L) = Recip - 1018
ODF_Array(L) - ODF - 1019
Next L - 1020
End
```

Fig. 10

```
(Continued from figure 9, step 945) - 1100
For L = 0 to NumberOf Segments - 1101
`select XRD data for segment L
Sspectrum = SegmentXRDpattern(L) - 1102
`initialize dTrace anddTraceCounter
For I - 0 to Max_d - 1103
dTrace(I) = 0 - 1104
dTraceCounter(I) = 0 - 1105
Next I - 1106
For 2θ = 0 to θSize - 1107
For γ = 0 to γSize - 1108
`retreve spectrum from element on "sphere" data
structure BinSet - Sspectrum(2θ,γ) - 1109
For I - 0 to NumberOfBins - 1110
`get photon counts from bin Counts = BinSet(I) -
1111
`calculate λ for particular bin
λ - MCAbinLambda(I) - 1112
`correct for radiation source spectrum variation
BetterCounts = Counts/SourceSpectrum(λ) - 1113
Calculate "d" spacing d = λ/(2*Sin(θ)) - 1114
`sum in data to intensity vs "d" trace
dTrace(d) += BetterCounts - 1115
`increment corresponding counter
dTraceCounter(d) +=1 - 1116
Next I - 1117
Next γ - 1118
Next 2θ - 1119
`take average For I = 0 to Max_d - 1120
DTrace(I) /= dTraceCounter(I) - 1121
Next I -1122
`store trace in array of traces
dTraceArray(L) - dTrace - 1123
Next L - 1124
END
```

Fig. 11

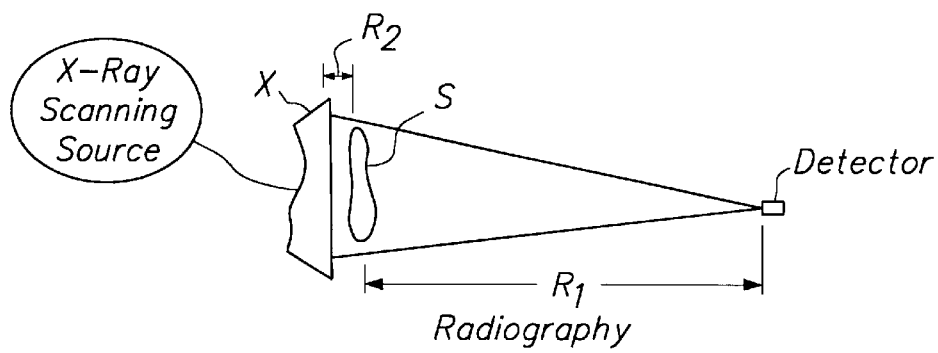
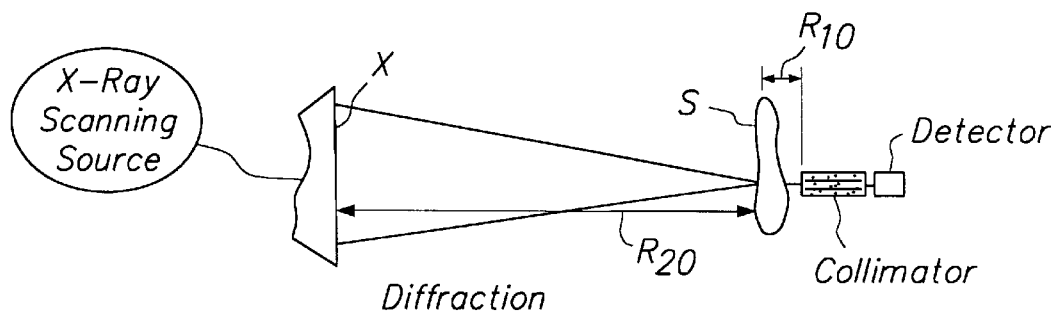
FIG. 13

METHOD AND APPARATUS FOR DIFFRACTION MEASUREMENT USING A SCANNING X-RAY SOURCE

BACKGROUND OF THE INVENTION

Previous to this invention, X-ray diffraction (XRD) measurements were made in a slow and tedious manner. FIG. 1 shows a schematic of the prior art, a typical X-ray diffraction apparatus. It comprises an X-ray source A, a collimator B, a specimen C, and an x-ray detector D. In the prior art the collimator is attached directly adjacent to the x-ray source. The collimator B changes the wide-angle output of the X-ray source A into a narrow beam. The x-ray beam E is aimed towards the specimen. The beam of X-rays E interacts with the specimen C. Some of the X-rays are diffracted by the specimen and are redirected towards the detector D. The X rays pass through the aperture F prior to entering the detector D. The characteristics of the diffracted X-rays are subject to mathematical description.

The Bragg Equation

The Bragg Equation:

$$n\lambda = 2d(\sin \theta) \quad (1)$$

describes X-ray diffraction. Lambda, $\lambda$, is the wavelength of the diffracted X rays in Angstroms. Theta, $\theta$, is ½ of the diffraction angle $2\theta$, which is the angle between the incident and diffracted X rays. The crystalline lattice plane spacing is "d", in Angstroms. For non-crystalline materials "d" is the interatomic spacing. The order of diffraction is an integer, "n". For diffraction, "n" is never less than 1. It is well known in the art that for X-ray diffraction to occur, lambda, theta, and d must have the relationship described by the Bragg equation.

In the typical XRD apparatus, the x-ray source and its collimator remain fixed. The X-ray wavelength, $\lambda$, is limited to a single value. The point detector and/or the specimen are moved. The angle $2\theta$, is thus measured allowing the detection of the various "d" spacings present in the specimen. Alternatively, $2\theta$ may be held fixed and the wavelength, $\lambda$, varied. The prior art XRD apparatus may be utilized in one of the following XRD methods.

Powder Method

The XRD apparatus may be used with a powdered or polycrystalline specimen. It is assumed in the analysis that the crystallites of the powdered specimen are randomly oriented and that there are a great many crystallites illuminated by the incident beam. This allows the detector to be scanned in one dimension rather than two-dimensions. If the crystallites in the specimen are not randomly oriented, the emerging diffraction pattern will not be a series of uniform rings, but a constellation of spots or perhaps mottled rings. A linear scan would not correctly gather all the information contained in these mottled rings or spots. Specimen preparation for this type of analysis is time-consuming and requires skill and care.

When a specimen has few crystallites, or non-random orientation of its crystallites, the specimen can be rotated about one or more axes during the test. This simulates a specimen with random crystalline orientation distribution. However, the required movement often increases the time needed to perform the test. The data collected during a test where the specimen is rotated may be collected in a manner that preserves the rotation orientation information. The preferred crystalline orientation (also known as "texture") may be sensed using this technique.

Laue Equations and Method

The Laue method exploits the full, three-dimensional nature of X-ray diffraction. The Bragg equation is a simplification of the three-dimensional Laue Equations:

$$a1 \cdot (S-So) = h\lambda \quad (2)$$

$$a2 \cdot (S-So) = k\lambda \quad (3)$$

$$a3 \cdot (S-So) = l\lambda \quad (4)$$

X rays diffracted from a single incident beam, So, are diffracted in three-dimensions, not just in a single plane. The directions of the incident and diffracted beams are represented by So and S, respectively. The crystal lattice vectors are a1, a2, and a3. The Miller indices are h, k, and l. The variable $\lambda$ is wavelength, as it is for the Bragg equation, (1).

In the Laue method, the broad-spectrum ("white") X-ray source is collimated to a thin, pencil-like beam. A specimen, usually a single crystal, is placed in the path of the pencil x-ray beam. X rays are diffracted by the specimen and emerge in a variety of directions, as described by the Laue equations. A sheet of photographic film, or some other area detector, is placed near the specimen. The sheet of film may be placed behind the specimen, between the specimen and the X-ray source, or nearly anywhere as required by an operator and as dictated by the application. X rays that are diffracted by the specimen travel to the film and produce a "Laue pattern." If the specimen is a single crystal, the Laue pattern is a set of small spots. The film (or a typical position-sensitive area detector) does not record wavelength information, only intensity and location information. By knowing the relative location and orientation of the X-ray beam, the specimen, and the plane of the film, it is possible to accurately calculate $2\theta$ for each of the spots.

Since there are usually a great many spots on the film, it is possible, by trial and error, to ascertain the crystalline orientation of the specimen, the crystal structure of the specimen and the dimensions of the crystal unit cell. However, it can be a tedious process.

Since film, and other position-sensitive area detectors cannot achieve high resolution for both position measurement and wavelength measurement, the Laue method is used principally on single crystals. This is because, without wavelength information, it is impossible to use the trial-and-error method if more than one crystal is illuminated by the X-ray beam. The lack of a practical means of gathering wavelength information as part of a Laue measurement severely limits the application of this method.

Area Detectors Vs Point Detectors

An "area" detector is sensitive to X rays in a plane, generally oriented normally to the diffracted X-ray beam. A line detector can also be scanned to function as an area detector. Typically, area detectors are not able to measure the wavelength of the X rays, only the intensity and position within the detector plane.

A "point" detector, as it is known in the art, is insensitive to position within its sensing region. The detector does not detect X-rays at an actual point, but over its volume. It does not distinguish where, within its volume, the X-ray photon was detected. Point detectors are often "energy-discriminating." That is, they produce a signal that can be processed to determine the wavelength of the detected X-ray photon.

Mono-chromatic vs. "Color" Detectors

An "area" X-ray detector may be substituted for the "point" X-ray detector described in the XRD methods above. An area detector is sensitive to X rays in a plane, generally oriented normally to the incident X-ray beam, rather than a single point. While point detectors can be made to detect both the wavelength and the intensity of X-rays, area detectors typically only sense the intensity. These detectors are mono-chromatic as to output signal and are known as "black and white" detectors. Area detectors have been produced that detect both X-ray intensity and wavelength. These are referred to as "color" area detectors. However, there is a fundamental compromise between spatial resolution and wavelength resolution. These "color" X-ray area detectors are very expensive.

If the orientation of a single crystal of a known substance is sought, a "black and white" area detector can be used. Since the "d" spacing of the substance is known and limited to a few values, the spots (of unknown wavelength) appearing on the area detector may be correlated to crystal lattice planes by a trial and error process. Thus, the orientation of the crystal may be determined.

The common thread of all of the prior art XRD apparatus is that the X-ray source is fixed in space and its output is collimated.

Recordation of Diffracted X-Rays

Recording the diffracted X rays in the prior art generally involves using photographic film to record the detected X-rays' images, regardless of their wavelength. However, use of photographic film for obtaining X-ray diffraction images such as Laue patterns has several disadvantages. The Laue pattern image is not immediately available because of the need to develop the film. Further, exposure time is prolonged as a majority of the X rays do not interact with the film. Fluoroscopic screens enable instant viewing of an image but have the disadvantage of requiring a darkened room for human eye viewing.

Efforts to resolve the problems associated with older X-ray imaging techniques have included use of an image intensifier and video imaging chain to generate a visible image on the screen of a display monitor. However, this produces a third generation image, which tends to be degraded by electronic noise. The first generation image appears on a fluorescent screen at the input of the image intensifier. The second generation image appears at another fluorescent screen at the output of the intensifier. The third generation image is produced by a video camera that views the image intensifier output. In order to improve image quality, the electronic signal generated by the image intensifier can be digitized to enable computerized image enhancement but this produces only marginal improvement.

In some more recent XRD systems, the image intensifier system is replaced with an array of minute electronic X-ray detectors such as charge coupled devices (CCD's). Data for constructing the image is read out of the CCD array on a pixel by pixel basis to provide an image, which may be displayed at the screen of a video display monitor. Of particular importance in utilizing a CCD array for acquiring X-ray diffraction imaging data is the small field of view of the CCD. The small field of view limits the angular range of the diffracted X rays the CCD is capable of detecting. Other position sensitive large area detectors suffer from lack of good spatial resolution and are very expensive.

Fundamental Differences between XRD and Radiography

In radiography, a shadowgraph, or radiograph, is made of the specimen by passing X rays through the specimen and detecting the directly transmitted rays that have not been absorbed or scattered by the specimen. The resultant shadowgraph resembles the physical shape of the specimen. The wavelength of the detected X rays is of little or no interest. As long as a large portion of the incident X rays are energetic enough to pass through the specimen, no thought is given to wavelength. X rays that do not take a direct path from the source to the detector are considered highly undesirable. A strong effort is made to prevent, or at least suppress, these nuisance rays from reaching the detector. The hardware in a radiographic system is specially fashioned and arranged to enhance the detection of directly transmitted primary rays and to strongly suppress detection of indirect, scattered, secondary rays.

An X-ray diffraction apparatus is quite different. The system components are fashioned and arranged to strongly suppress detection of the direct, primary radiation and to enhance the detection of indirect, secondary radiation. This is the complete opposite of a radiographic system. An XRD apparatus produces a pattern or a plot not a shadowgraph. The pattern or plot contains little or no information about the physical shape of the specimen. The pattern or plot instead reveals information about the atomic spacing and crystalline structure in a small region of the specimen.

The wavelength of the diffracted X rays is a key part of x-ray diffraction measurements. Most XRD systems restrict the source to a single wavelength, carefully sort the diffracted rays in terms of wavelength, or both. Only the traditional Laue method does not explicitly measure or restrict wavelength, but only single crystals can be analyzed using the traditional Laue method because wavelength information is not available. A tedious trial-and-error method must be used in lieu of wavelength information. If wavelength information could be recorded as part of a Laue measurement, it would no longer be restricted to use on single crystal specimens, but would have very broad application.

Devices representative of the art are:

U.S. Pat. No. 5,684,857 (1997) to De Bokx discloses a method for GE-XRF X-ray analysis of materials and apparatus for carrying out the method. FIG. 1 shows an X-ray source 4, a front collimator 14, specimen 16, back collimator 18, and detector 20.

U.S. Pat. No. 5,481,109 (1996) to Ninomiya et al. discloses a surface analysis method and apparatus for carrying out the same (see FIGS. 1, 7–16).

U.S. Pat. No. 5,457,727 (1995) to Frijlink discloses a device for processing a measured signal corresponding to the intensity of X rays reflected by a multi-layer structure on a substrate. FIG. 7 shows an X-ray source 1, a collimator system 2 and 3, a goniometer specimen support 9, a collimator system 5, and a detector 8.

U.S. Pat. No. 5,384,817 (1995) to Crowther et al. discloses an X-ray optical element and method for its manufacture. FIG. 1 shows an X-ray optical element and method for its manufacture. FIG. 1 also shows an X-ray source 12, a sample 16, a device 20 (which can be a collimator), a reflective element 22 and a detector 24. This figure is analogous to the typical arrangement as shown in FIG. 1 of the present application.

U.S. Pat. No. 5,267,296 (1993) to Albert discloses X-ray images produced on a monitor display screen by situating the subject between a detector having a minute X-ray-sensitive area and an X-ray source having an extensive anode plate on which an X-ray origin point is swept in a raster pattern similar to the raster of the display monitor.

U.S. Pat. No. 5,263,075 (1993) to McGann et al. discloses a high-annular resolution X-ray collimator. FIGS. 1–2 show an X-ray source 10, a slit collimator 20, and detectors 32.

U.S. Pat. No. 5,008,910 (1991) to Van Egeraat discloses an X-ray analysis apparatus comprising a sagittally curved analysis crystal. FIG. 1 of Van Egeraat shows a laser source 2, a specimen 6, an analysis crystal 8, a collimator 18, and a detector 16. This figure shows similar arrangement as shown in FIG. 1 of the present application.

U.S. Pat. No. 4,896,342 (1990) to Harding discloses an X-ray apparatus, which irradiates an examination zone in different positions by means of a primary beam having a small cross-section and a detector on the other side of the zone to measure the scattered primary beam.

U.S. Pat. No. 4,887,285 (1989) to Harding, et al discloses a method of determining the share of different chemical elements in an examination zone.

U.S. Pat. No. 4,850,002 (1989) to Harding et al discloses a two dimensional Compton profile imaging method and apparatus.

U.S. Pat. No. 4,104,519 (1978) to Oldendorf discloses a method and apparatus for retrieval of exposure information from film images. FIG. 5 shows a raster derive circuit 20, a source 12, a collimator 14, a filter 32, a film 16, and detector 26.

U.S. Pat. No. 3,949,229 (1976) to Albert discloses radiographic images of high definition and clarity produced quickly and with reduced radiation exposure of the subject by utilizing a scanning X-ray source in which a moving point source of X rays is created by sweeping an electron beam in a raster pattern on a broad anode.

U.S. Pat. No. 3,885,153 (1975) to Schoeborn et al. discloses a multi-layer monochromator. FIG. 2 shows two annular slits to produce a collimated neutron beam 13, a monochromator crystal 11, and a detector 15.

U.S. Pat. No. 3,373,286 (1968) to Han discloses a device for measuring the characteristics of a material moving on a conveyor with means for minimizing the effect of flutter. FIG. 1 shows a radiation source 2, a material 3, (which can be made of metal, plastic, etc. Column 3, lines 55–60), a collimator 12 and a detector 4. This patent shows similar arrangement as required in the reverse geometry embodiment of the FIG. 1 of the present application.

Recently, systems have been made available which provide for the movement of the X-ray source while the detector remains in a stationary position. These are unlike the foregoing fixed X-ray source systems. U.S. Pat. No. 3,949,229 ('229) to Albert is representative of such prior art. Albert '229 utilizes an X-ray generating component wherein a moving point source of divergent X rays is produced by scanning a broad area target plate with a charged particle beam. A relatively very small area radiation detector is spaced apart from the source to intercept X rays, which have passed through the subject undergoing examination. The output of the detector is used to control a cathode ray display tube or the like, having a raster pattern coordinated with that of the X-ray source, to produce a visual radiographic image of the subject. The detector output signals may also be stored on magnetic tape or by other means for later reconstruction as an image. Various electronic image enhancement techniques may readily be applied if desired. Automatic brightness control is provided in some forms of the Albert 229 invention to further reduce radiation dosage and to provide a more uniform contrast throughout different areas of the image by feeding back an average image intensity signal to the X-ray source to vary X-ray output in the course of the scanning as required for this purpose. Stereoscopic images may be produced by using two small area X-ray detectors which are spaced apart with each controlling separate visual images that are viewed by separate eyes of the observer or, in another form of the invention, by utilizing a single detector controlling the two separate images alternately wherein the raster pattern area at the X-ray source is alternately shifted between two at least partially separate areas of the target plate of the source.

Yet another invention representative of the art is U.S. Pat. No. 5,267,296 ('296) by Albert. In one aspect, Albert '296 provides X-ray imaging apparatus having an X-ray source which includes an anode plate, means for directing an electron beam to the plate to produce X-rays at an X-ray origin point on the plate, and means for traveling the X-ray origin point in a raster scanning motion within a first raster scan area on the plate in response to an x-axis sweep frequency signal and a y-axis sweep frequency signal. An X-ray detector produces a detector signal that is indicative of variations of X-ray intensity at a detection point that is spaced apart from the anode plate. A monitor has an image display screen and means for moving a visible light origin point in a raster scanning motion within a second raster scan area at the screen. The intensity of the light origin point is modulated during the course of the raster scanning motion at the second raster scan area by the variations of the detector signal which occur during the course of the raster scanning at the first raster scan area. The apparatus further includes means for producing a first sequence of digital data bytes which encode successive values indicative of variations in the magnitude of the x-sweep frequency signal that are to occur during the course of the raster scanning at the first raster area, means for producing a second sequence of digital data bytes which encode successive values indicative of variations in the magnitude of the y-sweep frequency signal that are to occur during the course of the raster scanning at the first raster area. Also included is means for producing the x-sweep frequency signal and the y-sweep frequency signal during the course of the raster scanning at the first raster scan area by conversion of the values encoded by successive data bytes of the first and second sequences into analog signals. Means are provided for producing and storing digital signals, which encode the location of a selected area of the image in response to area of interest selection controls. Further components include means for reducing the size of the first raster pattern at the anode plate in response to a zoom signal and means for positioning the reduced first raster pattern at a location on the anode that corresponds to the selected location on the image display screen that is encoded by the digital signals. Albert '296 provides a method for creating a radiographic image of a subject, which includes the step of scanning an electron beam in a first raster pattern on an anode plate to produce a moving X-ray origin point. X rays are detected at a detection point situated at the opposite side of the subject from the anode plate and a detector output voltage is produced in response to the detected X rays. Further steps include sweeping a light origin point on a display screen in a second raster pattern and varying the intensity of the light origin point at successive points in the second raster pattern in accordance with variations of the detector output voltage at corresponding points in the first raster pattern, selecting an area of the image at the display screen for magnification, encoding the location of the selected area in digital signals and initiating a zoom signal. Still further steps in the method include reducing the size of the first raster pattern in response to the zoom signal and positioning the reduced first raster pattern at a location on the anode plate that corresponds to the location in the image that is encoded in the digital signals. Albert '296 enables faster operation of reversed geometry scanning X-ray systems, simplifies the operator's control manipulations and expands the capabilities of the system with respect to producing images of different types by enabling digital data processor control of the scanning X-ray source and image characteristics. The operator may, for example, zoom in to magnify one or more areas of the image that are of particular interest by simple actuation of one or more standard computer input devices. High resolution scanning of the subject can be limited to selected regions, which are of interest, thereby reducing scanning time and minimizing radiation exposure of the subject. Magnified high definition images of selected regions of a subject can be acquired, stored, digitally enhanced in any of various ways and then be displayed sequentially or simultaneously. Albert '296 enables variation of the aspect ratio or height to width ratio of the image in response to digital signals to facilitate imaging of differently shaped subjects or, in the case of a moving subject, to compensate for an image distortion, which can otherwise result from the motion of the subject.

BRIEF SUMMARY OF THE INVENTION

The primary aspect of the invention is to provide an XRD diffractometer using a scanning X-ray source.

Another aspect of the invention is to provide an XRD diffractometer having an X-ray detector with a collimator.

Another aspect of the invention is to provide an XRD diffractometer wherein the movement of the scanning X-ray source and the detector is correlated.

Another aspect of the invention is to provide an XRD diffractometer capable of performing XRD analysis of a specimen in three dimensions simultaneously.

Another aspect of the invention is to provide an XRD diffractometer having controllable modulation of the Bragg angle.

Another aspect of the invention is to provide an XRD diffractometer giving non-destructive phase identification of a specimen.

Another aspect of the invention is to provide an XRD diffractometer giving complete texture determination non-destructively.

Another aspect of the invention is to provide an XRD diffractometer having high throughput allowing quick analysis of specimens.

Another aspect of the invention is to provide an XRD diffractometer having good spatial resolution.

Another aspect of the invention is to provide an XRD diffractometer having high sensitivity.

Another aspect of the invention is to provide an XRD diffractometer having good wavelength resolution.

Another aspect of the invention is to provide an XRD diffractometer having simplified control manipulations by an operator.

Another aspect of the invention is to provide an XRD diffractometer giving real-time XRD analysis.

The invention comprises a scanning X-ray source, a specimen, a collimator, and a point detector. A neutron or gamma ray source could be used in addition to an X-ray source. The X rays leave the source and travel towards the specimen. Some of the X rays are diffracted by the specimen at the proper angle to travel through the collimator and to the detector. The geometry of traditional XRD methods is thus reversed in the present invention.

In this embodiment of the invention x-rays leave the scanning radiation source, are diffracted by the specimen, and enter the detector via the collimator. The primary beam from the X-ray source is selectively excluded from entering the detector. The location of the source and the orientation of the collimator establishes the angle two theta, $2\theta$. The detector can detect the intensity and/or the wavelength of the diffracted X ray. All information needed to solve the Bragg equation is available. The elegance of this geometry is that the detection tasks and the angle determination tasks are completely separated. The angle information, $\theta$, is provided by the position of the scanning radiation source with respect to the specimen and the collimator on the detector. The angle can be rapidly modulated by moving the source. No motion of the detector is needed. The detector need only determine the intensity (and wavelength) of the diffracted x-rays. The detector need not be position-sensitive as it would be if the X-ray source were collimated and a traditional geometry used as in the prior art. The detector may be easily and inexpensively optimized for sensitivity in either intensity, or wavelength determination or both. If an electronically-scanned source is used, no part of the apparatus must physically move to perform XRD measurements. Moving-source XRD allows good spatial resolution in two or more dimensions, high sensitivity, good wavelength resolution and rapid data acquisition.

The invention discloses a new technique for producing Laue patterns that include high-resolution wavelength information. Thus, the full, three-dimensional, Laue equations may be applied to XRD measurements. Now that the prior missing wavelength information, $\lambda$, is available with this invention, each diffracted ray may be independently used to determine the atomic spacing "d". The trial-and-error method, of the prior art, is no longer required. Thus, this enhanced Laue method may be effectively applied to not just single crystals, but to a very broad range of specimens.

Any type of XRD measurement may be performed by the present invention. Chemical (phase) analysis is an example of an XRD measurement that can be performed. Texture (anisotropic crystalline orientation) measurements are another example of an XRD measurement that can be performed. Multiple detectors can be used, or, an array of detectors could be used. Further, the X-ray source may be scanned in two or three dimensions. The X-ray source may, or may not, have collimation or associated optics. A neutron or gamma ray source could be used in place of an X-ray source. Any manner of optics may be used for the X-ray detector(s). Capillary bundles are an example of an X-ray optic that could be used instead of a simple collimator. Neither the specimens) nor the detector(s) nor the optics must remain fixed in space in order to perform the method described herein. The source, however, never remains fixed with respect to the collimator and detector. As long as the position of each of these elements is known or measured, and can be correlated with the output of the detector(s), Bragg and other XRD calculations can be made. Thus, all the information needed for XRD measurements is available.

B. D. Cullity, on page 98 of his classic textbook "Elements of X-Ray Diffraction"; Addison-Wesley Publishing Company, Inc.; Reading Mass.;1978, writes: "The powder method is, of course, the only method that can be employed when a single-crystal specimen is not available, and this is the case more often than not in metallurgical work." The "Dube'-Albert" geometry for XRD analysis as disclosed in the present application makes this statement no longer true.

The present invention is based on the concept of moving X-ray source X-ray diffraction, unlike conventional x-ray diffraction systems, it can simultaneously provide both superior spatial and wavelength resolution over a large range of diffraction angles. This reversed geometry provides a number of advantages. The rate of throughput is considerably greater than conventional systems. Electronic movement of the source is much more rapid than the mechanical movement of the detector typically found on a conventional XRD apparatus. By using a multi-channel analyzer with a high-resolution, energy-sensitive detector, a large spectrum of diffracted X rays may be gathered simultaneously and with great sensitivity. Conventional XRD apparatuses typically reject all X rays but those of a specific wavelength, thus greatly increasing the time needed to gather the same equivalent XRD information. Radiation exposure of the specimen is greatly reduced as the electronic detector responds to incoming x rays with much higher efficiency than a photographic film or a fluoroscopic screen. The invention can also be relatively uncomplicated and inexpensive in comparison with other forms of X-ray diffraction equipment. To implement a fixed-source forward-geometry system that gathers the same XRD information would require a large array of many thousands of small, high-resolution, energy-sensitive detectors. A similar array of detector control electronics would also have to be constructed. It would be completely impractical to do such a thing.

The scanning X-ray source XRD method also enables magnification of an area of the XRD pattern produced by a specimen (which in reverse geometry is equivalent to a particular angular range of diffracted X rays) without movement of the specimen. The angular range of X rays diffracted at a particular region of angles can be selected by panning the raster area that has been reduced to provide the magnification. This capability provides enhanced resolution of the selectable angular range of diffracted X rays or Laue spots.

Differences Between Reverse-Geometry Radiography and Moving-Source XRD

In essence, the only thing that X-ray radiography and X-ray diffraction measurements have in common is that they both involve the use of X rays. In X-ray radiography, "primary" X rays are sensed by the detector. Primary x-rays are those that pass directly from the source through the specimen to the sensing device, i.e., film. X rays that are bent or scattered and thus do not take a direct path ("secondary" X rays) are undesirable in radiographic systems. Secondary X rays reduce the clarity, dynamic range, and overall quality of radiographic images. A great deal of effort is spent suppressing secondary X rays in radiographic systems.

The reverse-geometry radiographic system referenced in the prior art is specifically designed to be preferentially sensitive to primary X rays. All secondary X rays are considered to be undesirable. The prior art system produces an x-ray attenuation image or "shadowgraph" of an object placed between the source and the detector. The image is representative of the geometry and relative density of the object.

There are two types of secondary X rays. There are incoherently scattered X rays. Compton scattering is an example of incoherently scattered X rays. There are also coherently scattered X rays. These are called "diffracted" X rays. XRD measurement systems are designed to suppress the detection of primary X rays and to selectively detect diffracted X rays.

The present invention is designed to perform the opposite task as the reverse-geometry radiographic system in the prior art. The present invention is designed to selectively capture the diffracted portion of the secondary X rays. The detection of primary X rays is strongly suppressed in this invention. Unlike the reverse-geometry radiographic system, the data gathered, and thus any image formed by a scanning source XRD system, contains information about the atomic spacing and crystalline orientation of the specimen (object under analysis.) Unlike a radiograph, the XRD pattern displayed by the instant invention has no resemblance to the physical appearance or shape of the specimen.

Since the scanning source XRD system detects secondary, not primary, X rays, the detector and x-ray source need not be on opposite sides of the specimen. Further, the specimen need not be placed between the detector and the X-ray source. The X-ray detector(s) may be in any position in a spherical geometry along a radius relative to the specimen (s).

In scanning radiation source XRD, the detector system must be designed to select diffracted X rays in deference to primary X rays. A typical collimator designed for this function will have two apertures spaced some distance apart. This type of collimator only allows X rays to pass that fall within a very small solid angle. The primary X-ray beam is prevented from passing through this collimator to the detector.

As opposed to the instant invention, a detector collimator is optional on the reverse-geometry radiographic system. A detector collimator used in reverse-geometry radiography is designed accept X rays over a large solid angle. This large solid angle must subtend the entire source raster plane. If used, it is designed so that the primary X rays may easily pass, and secondary X rays are excluded to a large extent. As the detection surface is relatively minute in the a reverse-geometry radiography system, only a relatively very small proportion of the total secondary X-ray emission is detected. Thus, definition and clarity of the radiograph are greatly enhanced. While it is advantageous in some circumstances to provide a multi-apertured collimator between the X-ray source and the detector in a reverse-geometry radiographic system, undesirable secondary X-ray effects are greatly reduced even in the absence of such a collimator. The radiographic system is by no means dependent upon the presence of a collimator for operation.

Moving Raster-Plane Mode

The best mode is to translate the scanning X-ray source, in a controlled manner, in a direction substantially perpendicular to the X-ray source raster plane. The raster plane is the plane from which the x-rays are emitted. This will allow three-dimensional scanning of the X-ray source rather than simple two-dimensional scanning. The XRD information gathered during a three-dimensional scan can be processed via computed tomography (CT) algorithms, well known in the art.

Transmission Vs Back-Reflection XRD

The invention may be used to perform "transmission" or "back-reflection" XRD. In "transmission" XRD, the detector is on the side of the specimen opposite that of the X-ray source, i.e., the X ray as it is diffracted, is transmitted through the specimen. In "back-reflection" XRD, the detector is on the same side of the specimen as the X-ray source. Consequently, the X-ray detector(s) in the invention may be in any position along a radius of a line drawn through the specimen relative to the specimen(s).

Further, any size or number of specimens can be tested simultaneously using the invention. This is in large contrast to the prior art. Since X rays emerge from the source in all directions any large number of specimens can simultaneously be bathed with X rays from a single moving X ray source. Also, a very large specimen can be bathed in X rays from a single moving X-ray source. Detectors with their collimators can be aimed to detect diffracted X rays from many parts of a single specimen or from multiple specimens.

The term specimen is used here to refer to any substance, material, or object being analyzed using the invention.

X Ray Source Scanning Modes

It is possible to make a limited XRD measurement by scanning the X-ray source in only one dimension instead of two. The resultant XRD information so gathered will be reduced from the full three dimensions down to two dimensions. That is, the measurement will only reveal information relevant to a single plane rather than in all directions. In some applications, this limited information may be all that is needed.

Laue Pattern Imaging using Moving Source XRD

If the diffracted X rays, entering the detector, are not sorted in energy, a standard, black and white, Laue pattern results. The moving-source system disclosed herein may be used to image both traditional, "black and white" Laue patterns as well as "color" Laue patterns.

Moving Source Method

The moving radiation source method described herein may make a complete set of XRD measurements utilizing the apparatus of the present invention without moving the specimen. It also does not require that a powder be made of the specimen as required in the prior art. The invention also performs the analysis in real-time and can perform XRD measurements at many separate locations on a large specimen simultaneously, if desired. This is accomplished by aiming multiple collimator/detector sets at many locations on the specimen. Further, there is no requirement that the material being analyzed be uniform throughout as required in the prior art. Thus, the invention can sense any non-uniform properties present in a specimen. Since the specimen need not be rotated or moved, there is no need to prepare a special specimen to perform the measurement as there is in the conventional powder method described herein. In contrast to the prior art, the invention may be used to do a fast, non-destructive XRD measurement on a relatively large object by using multiple detectors and collimators and processing the data from these multiple detectors in parallel. The XRD measurement by each X-ray detector is independent and unaffected by all other X-ray detectors. Thus, the data from these additional detectors may be collected and processed independently of other detectors. Measurements may be made at many locations on a large object independently and simultaneously. The position of the source must, of course, be known by all of the parallel systems used to process detector data. This is because angle information must be correlated with the detector output to make XRD calculations. This is why parallel processing of the detector data stream is possible.

The X-ray source may be scanned by any number of methods. Electronically scanning the source (somewhat like a TV screen) is perhaps the best means of raster-scanning the X-ray source for this reverse-geometry measurement method. A very fast, reliable XRD measurement can be made by electronically raster-scanning the X-ray source. The raster scan may be of any geometric form; rectilinear, circular, trapezoidal or otherwise. It can be in three-dimensions as well.

Moving Specimen Mode

An example of the XRD analysis of a moving specimen would includes an arrangement where parts are passed on a conveyor in front of the fixed detector and scanning X-ray source. The X-ray source scans relative to the detector, but the specimen moves as well. The sensed volume in the part is somewhat elongated and blurred as the part moves. XRD information about the bulk material of the part is available even though the sensed volume is not as well-defined as would be if the part were motionless.

Another example of the XRD analysis of a moving specimen would be aluminum stock passing by the fixed detector and scanning X-ray source as it is extruded or rolled during fabrication. Again, the sensed volume is somewhat elongated, blurred, and not as well-defined as would be if the stock were motionless, but the XRD information gathered would be representative of the section of stock that passed by during the scan.

Yet another example of the analysis of a moving specimen would be an operating turbine engine. The position of the turbine shaft would have to be known at all times. Data from the detector would be gated with respect to a specific shaft position or positions. Just as a mechanic's strobe light "freezes" the timing marks on the crankshaft pulley, the turbine can be effectively "strobed" or gated by the system of the present invention to selectively gather XRD data at a specific shaft position in this engine. As long as the position of the moving part is known with respect to the location of the X-ray source and the detector, all the information needed for XRD analysis is available.

Moving Collimator Mode

As an example of a moving collimator, the collimator, or a plurality of collimators, with associated detectors may be scanned over an object. The raster plane of the scanning X-ray source may remain fixed or may move over the object in concert with the collimator(s).

The system as a whole, (scanning X-ray source, detectors and collimator(s)) may be moved across a specimen. The movement may be done incrementally or continuously. If done incrementally, the sensed volume of each detector/collimator set would be well-defined. The result would be a set of XRD measurements from specific well-defined regions of the specimen. If the movement were continuous instead, the sensed volume would be blurred or elongated. The result would be a set of measurements representing the average properties over these diffuse sensed volumes. Thus, XRD measurements may be performed in many places on the same object.

A very similar result may be obtained by moving the detector and its collimator (or multiple detectors with collimators) across a specimen, while holding the raster-plane radiation source fixed, relative to the specimen. The relative motion of the detector/collimator with respect the scanning plane would have to be measured or known so that angle information, $2\theta$, could be calculated as needed for XRD measurements. Otherwise, the operation of the system is the same as would be in the case (above) where the X-ray source raster plane and the detector/collimator were moved in concert.

In yet another mode, the detector remains fixed and, in a limited fashion, the collimator or a portion of the collimator is scanned over the specimen. This is just a slight modification of the cases above. The detector need not move if the collimator movement is limited. The limitation to this alternative is that the X-rays passing through the collimator must strike the detector volume. The collimator may be moved radially about the detector and/or translated to some extent.

As previously described, as long as the position of the collimator is known or is measured, all the information needed for XRD measurements is available. As long as the X-rays leaving the collimator strike the detector volume, the specific position of the detector is not relevant.

BRIEF DESCRIPTION OF THE SEVERAL VIEWS OF THE DRAWING

FIG. 6 is a flowchart showing the invention used to perform a texture measurement.

FIG. 7 is the flowchart showing the invention used to perform chemical analysis with the single wavelength process.

FIG. 8 is the flowchart showing the invention used to perform multiple-wavelength chemical analysis process using an multichannel analyzer (MCA).

FIG. 9 is a flowchart which illustrates the invention used to perform the computed tomography process.

FIG. 10 is a flowchart showing how the data obtained in FIG. 9 can be analyzed to obtain texture information.

FIG. 11 is a flowchart showing how the data obtained in FIG. 9 can be analyzed to obtain phase identification information.

FIG. 13 depicts the relative spacing of the source, specimen and detector for prior art radiography versus diffraction used in the invention of the present application.

Before explaining the disclosed embodiment of the present invention in detail, it is to be understood that the invention is not limited in its application to the details of the particular arrangement shown, since the invention is capable of other embodiments. Also, the terminology used herein is for the purpose of description and not of limitation.

DETAILED DESCRIPTION OF THE PREFERRED EMBODIMENTS OF THE INVENTION

Figure 1:
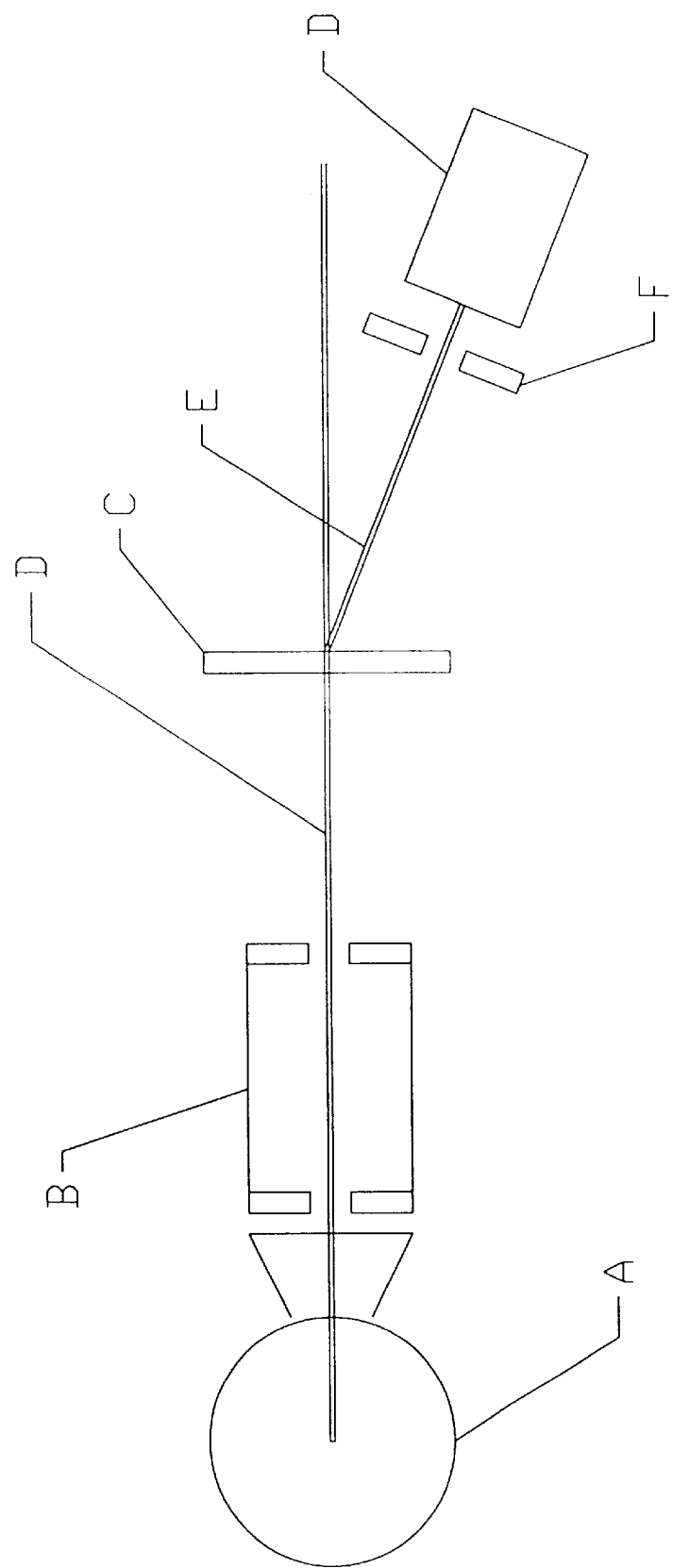
FIG. 1 shows a schematic of the prior art, a conventional transmission x-ray diffraction apparatus.

FIG. 1 shows a schematic of the prior art, a conventional transmission X-ray diffraction apparatus, which is discussed in the preceding sections.

Figure 2:
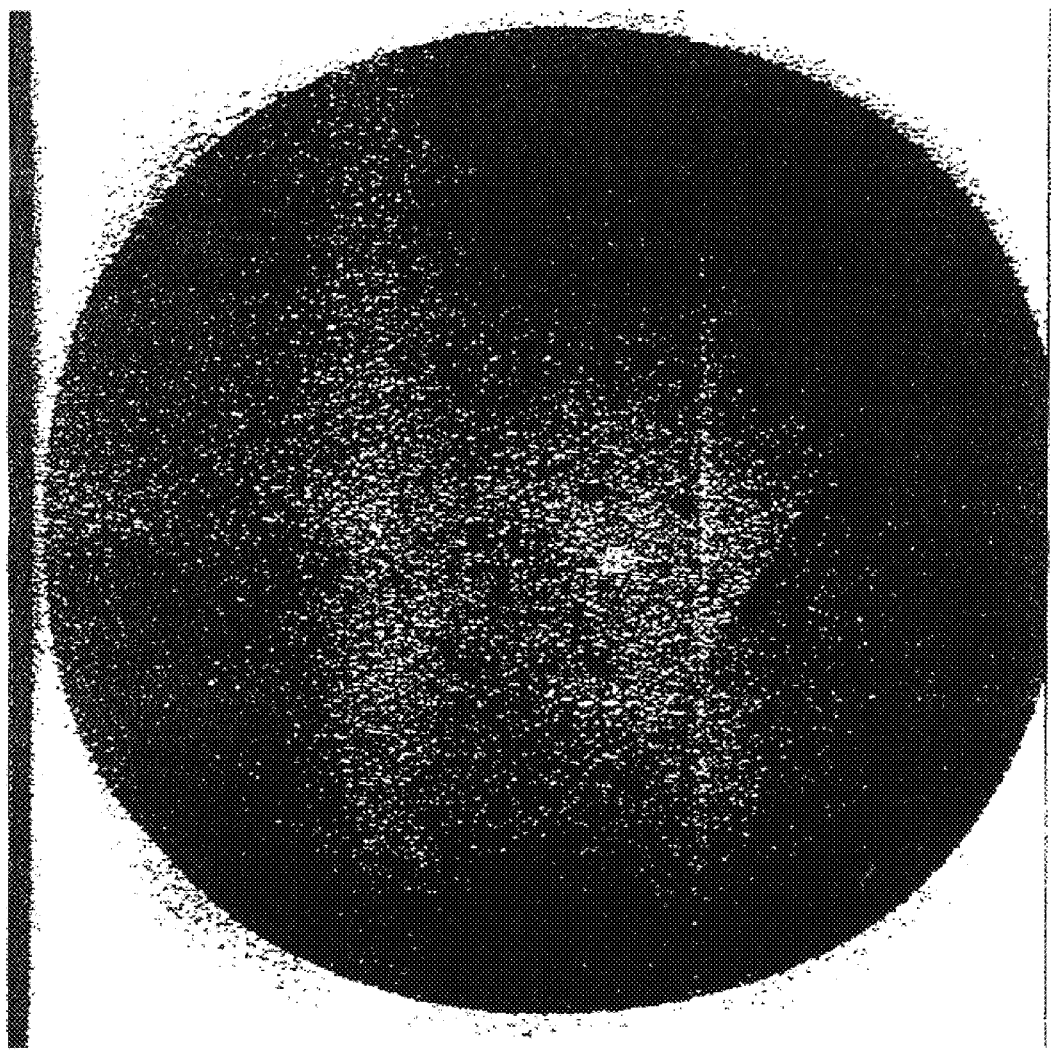
FIG. 2 is a Laue pattern obtained by use of the invention of the present application.
Figure 3:
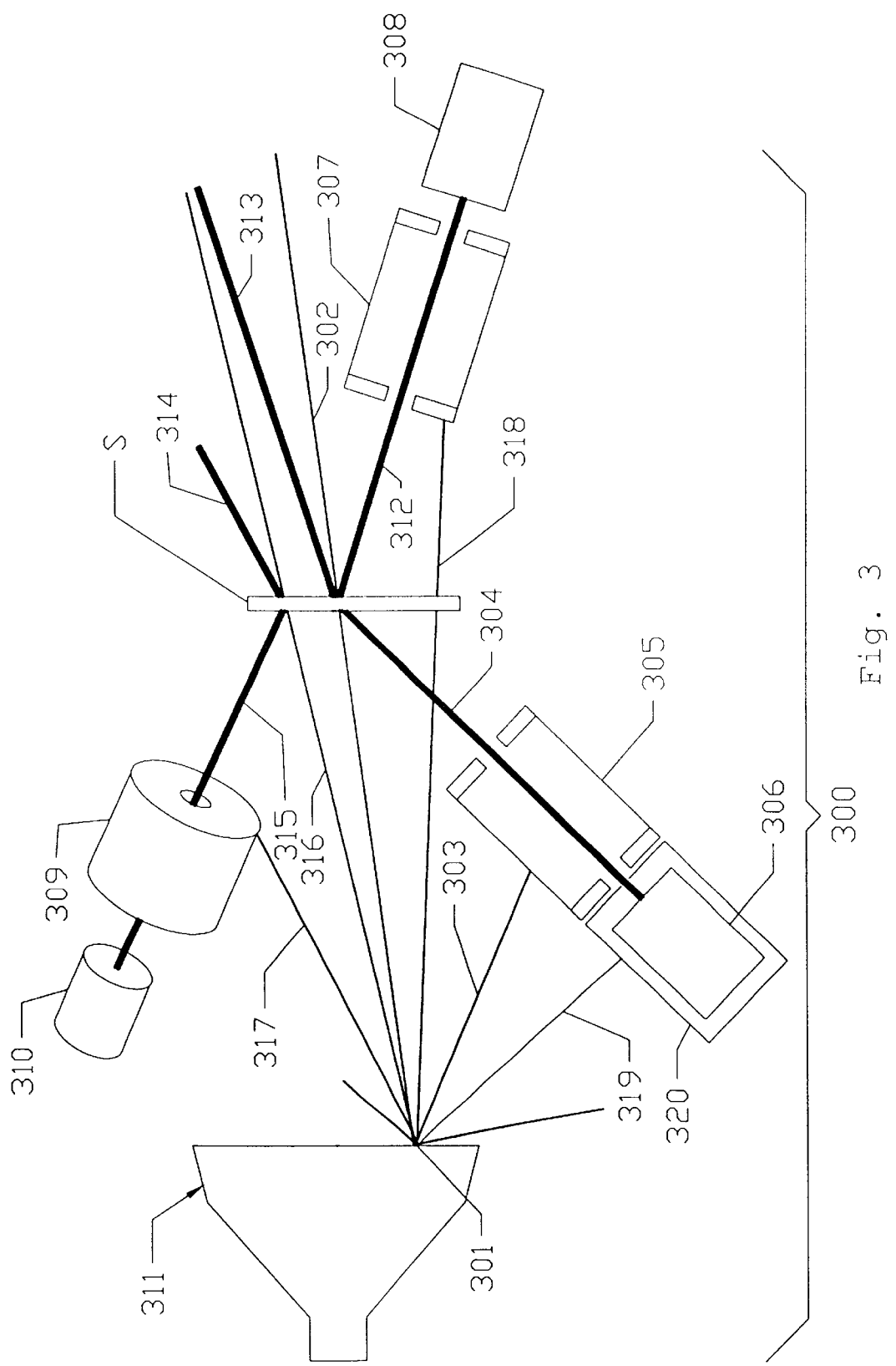
FIG. 3 shows a schematic of the reverse geometry X-ray diffraction system of the present application.

FIG. 2 shows a Laue pattern which was obtained using calcite as the specimen 303 in the system described in FIG. 3.

Referring to FIG. 3 of the drawings, a moving-source X-ray diffraction system 300 of the present invention is shown. System 300 includes a scanning X-ray source 301, an X-ray detector 306, and a collimator 305. A neutron or gamma ray source could be used in place of X-ray source 301. A specimen S is positioned such that primary X rays 302, 316 and 318 traveling directly from the scanning X-ray source 301 impinge upon it. The scanning X-ray source 311 causes the point of emission of the X rays 301 to move in a predetermined pattern. The collimator 305 and the detector 306 are positioned such that x-rays 304 diffracted from the primary X rays 302 by specimen 8 travel to the detector 306. The collimator 305 is fashioned and positioned such that most of the primary X rays 303 and 319 are blocked from traveling to the detector 306, the latter by shield 320. Primary X rays 317 and 318 are blocked from traveling to detectors 310 and 308, respectively. Since X rays are diffracted in all directions by specimen S, alternative positions and/or multiple detectors 308, 310 with corresponding collimators 307, 309 may be used. Diffracted X rays 312 and 315 are received by detectors 308 and 310, respectively. Diffracted rays 313 and 314 may also be detected (detectors not shown). In essence, the X-ray detector(s) may be in any position along any radius relative to a sensed volume of specimens. See FIG. 5 explanation for the discussion of the sensed volume hereinafter. The detector 306 may be one of the types known in the art which produces an output signal voltage that varies in accordance with variations of X-ray energy (wavelength) or simply intensity at the sensitive region. Detectors 306 may, for example, be a scintillation detector or germanium-lithium detector although other forms of detector may also be used.

Since the location of a detectors, 306, 308, 310, can be determined relative to the X-ray source, the value for $2\theta$ can be measured directly. With $2\theta$ known, the relationship between the wavelength X, and the atomic spacing "d," is set by the Bragg equation. The atomic spacing "d" maybe easily and unambiguously determined by sensing the wavelength $\lambda$ through processing the output of the detector 306.

Figure 4:
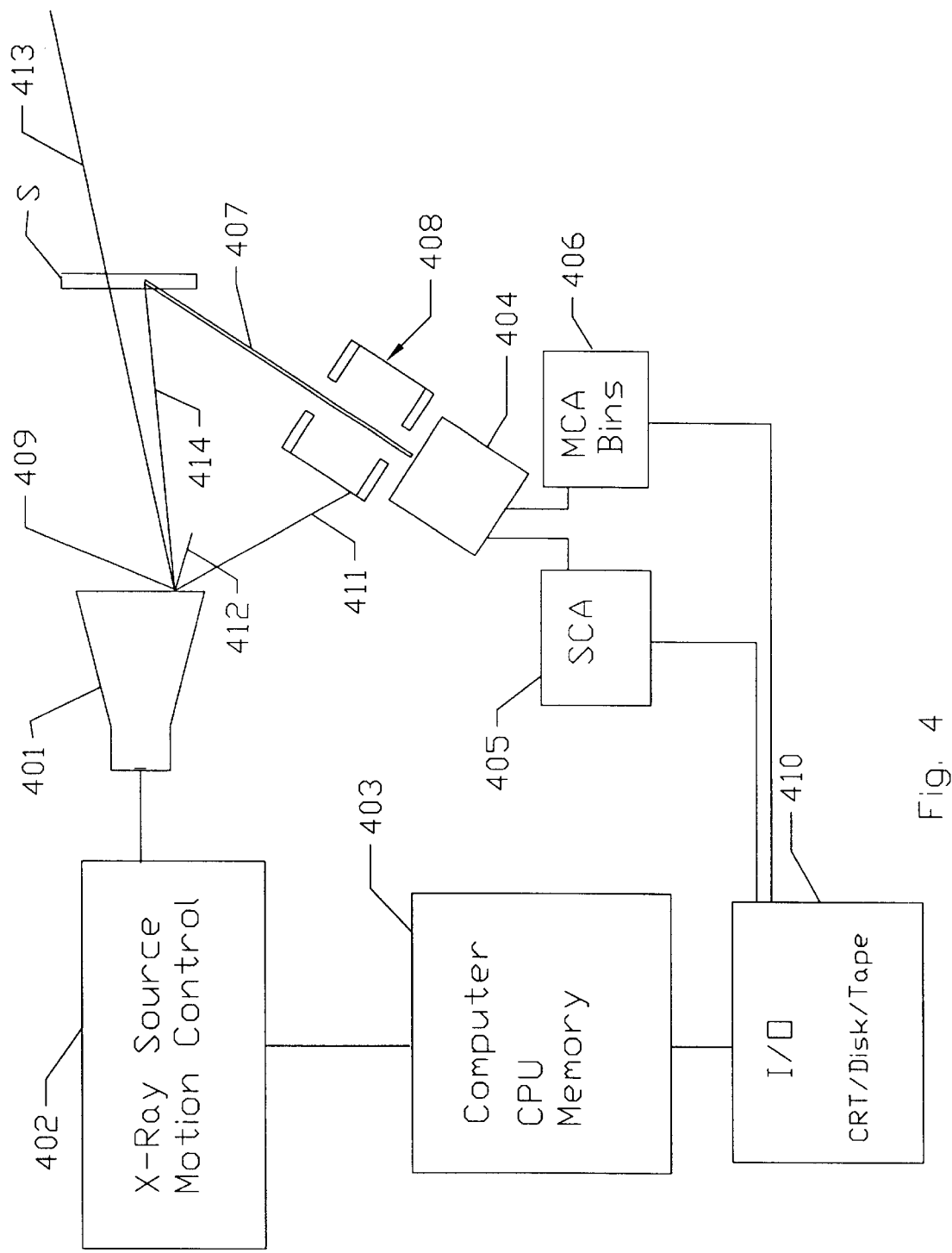
FIG. 4 shows a block diagram of the moving X-ray source made for the XRD apparatus of the present invention.

FIG. 4 shows a block diagram of the moving X-ray source mode of the invention. The scanning x-ray source 401 is controlled by the X-ray source motion control 402. The computer CPU 403 sends signals to the X-ray source motion control 402. The program and the programming signals control the motion of the X-ray source 401. These programming signals may also control the intensity and spectrum of the X-ray source 401 by altering the current and voltage supplied to the X-ray source, which may take the form of a tube. The scanning x-ray source sub-system consisting of source 401 and motion control 402 may be implemented by using components from a reverse-geometry X-ray radiographic system such as that described in Albert 229 and 296. The scanning X-ray source 409 emits X rays 411, 412, 413, and 414. The X rays 411 are of no interest and are excluded from the detector by collimator 408. X rays 414 are diffracted by specimen s creating ray 407, which is then detected by detector 404.

The computer 403 controls and interrogates the detector 404 via the detector electronics 405, 406. The detector electronics 405, 406 may be a single-channel analyzer (SCA) 405, and a multi-channel analyzer (MCA) 406. A simple event counter, or a simple rate meter may also be employed (not shown). Diffracted X rays 407 from the specimen S, that pass through the collimator 408 strike the detector 404. The detector 404 produces an electronic pulse that is processed by the SCA 405 or MCA 406. The height of the pulse from the detector 404 is inversely proportional to the wavelength of the X-ray photon that produced the pulse. The SCA 405 rejects all pulses from the detector 404 that do not fall within specified bounds. These bounds may be adjusted via electronic signals from the computer CPU 403 or via manual controls associated with the SCA 405 electronics. The output of the SCA 405 to the computer may be the numerical count of selected pulses or the count rate of pulses.

The MCA 406, is functionally a set of many SCAS. There is an array of electronic "bins" in the MCA 406. Each bin represents a selected portion of range of wavelengths. When a pulse arrives from a detector it is sorted by the MCA 406 in terms of height (1/wavelength) and placed in a corresponding bin. The contents of the bin corresponding to this wavelength, is incremented for each pulse received. The computer CPU 403 has access to this electronic array of memory bins. Thus the X-ray photons that strike the detector 404 are sorted by wavelength and are made available to the computer CPU 403.

The X-ray detector 404 and its associated control electronics 405, 406 are well known in the art. A single detector 404 with its associated electronics is shown. However, a plurality of detectors/collimators with associated electronics may be used in the invention.

The computer 403 gathers, correlates and processes information from the detector electronics 405, 406 and the X-ray source motion-control electronics 402. The computer CPU 403 presents this processed information to the user via the I/O 410.

A mechanical system may also be used for the scanning radiation source sub-system 401, 402 if desired. In an alternate embodiment of the invention, the electronically scanned X-ray source 401 is replaced by a relatively small X-ray source (not shown) which is mechanically scanned in a 2-D or 3-D pattern Standard, mechanical motion-control components, well known in the art, can be used to move an ordinary X-ray tube or isotope source in one, two, or three dimensions. These standard motion-control components typically are commanded by programming signals from a computer and deliver signals back to the computer regarding the position of the source. In an alternate embodiment, instead of moving the X-ray source mechanically, an X-ray absorbing plate with a small aperture may be mechanically moved, as above, in front of an X-ray source having a large area. The mechanical scanning of the X-ray source produces the same result as the electronically scanned X-ray source embodiment shown in FIG. 4.

Figure 12:
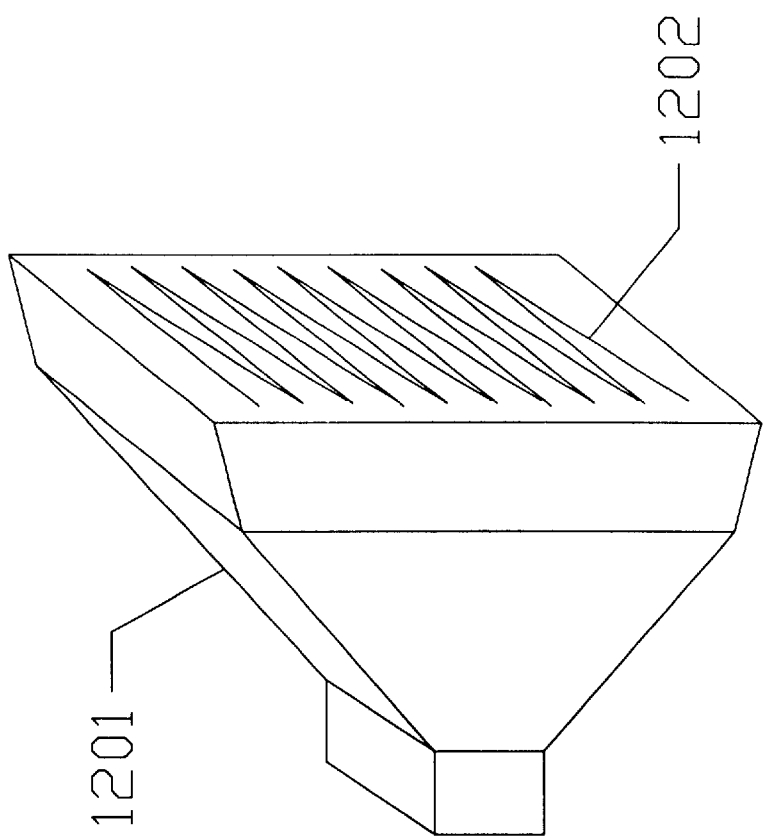
FIG. 12 depicts a raster scan used in the present invention.

The electronically raster-scanned X-ray source referenced previously, FIG. 12, may itself be mechanically scanned in a manner like that described above to add another dimension to the motion of the X-ray source. This allows the x-ray source to be effectively scanned in three-dimensions altogether. Typically, a mechanical motion control stage, known in the art, would be used to move the electronically scanned X-ray source in a direction roughly perpendicular to the raster plane. This motion control stage would typically be controlled and interrogated by the computer. Throughout this specification, the term "raster-scan" is used. However, it must be understood that this is one of any number of ways in which a scan may be performed and is meant as a generic two-dimensional scanning process. A spiral scan and a Monte-Carlo scan are two examples of alternative scanning methods that achieve the same final result of moving a radiation source point uniformly over a two-dimensional plane.

Figure 5:
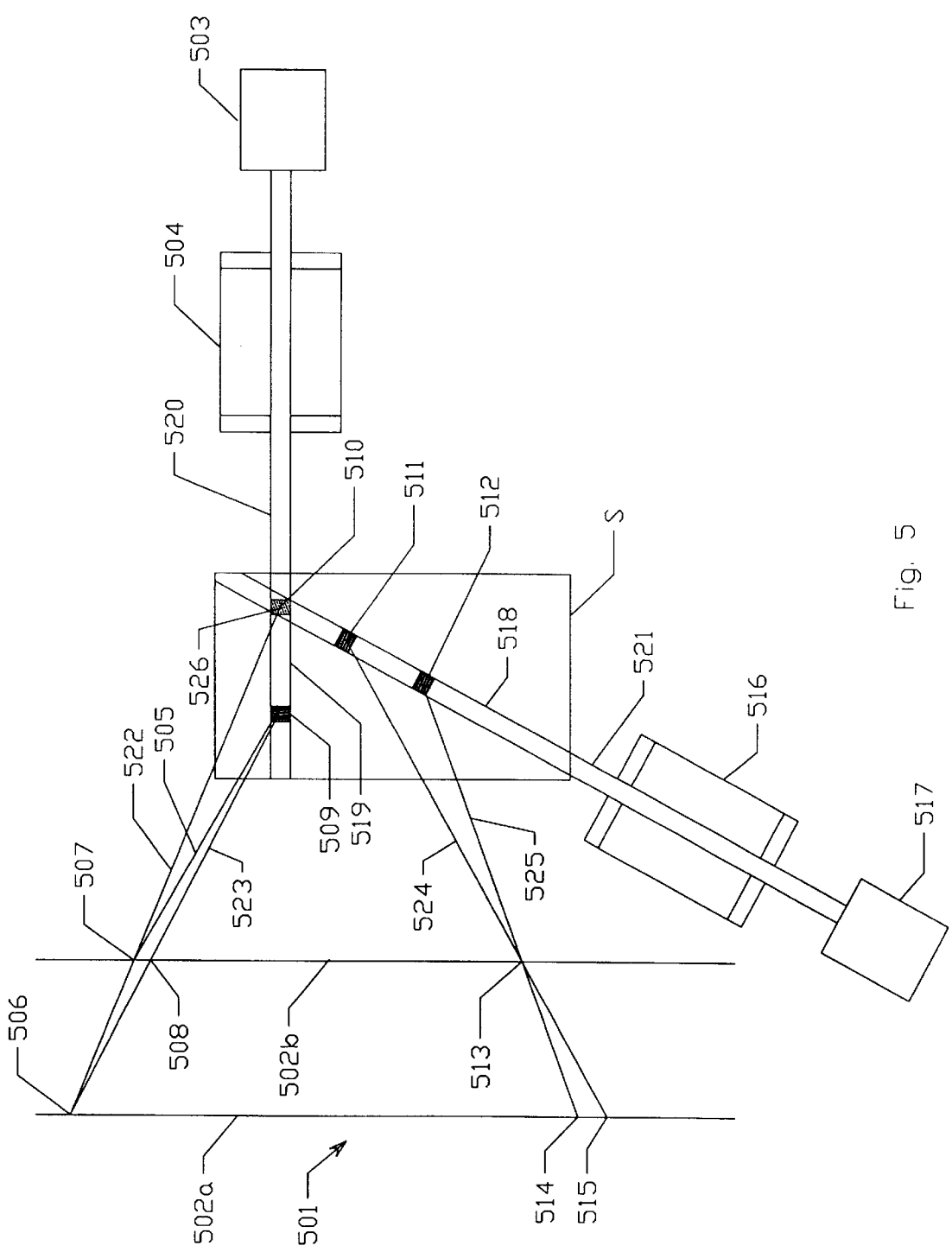
FIG. 5 is a schematic view showing how a three-dimensional X-ray source scan is used with the system of the present invention to isolate small segments of the specimen sensed volume.

FIG. 5 is a schematic showing how a three-dimensional radiation source scan is used to sense a specimen volume using small segments. The scanning plane of a raster-scanned source 501, is moved from raster plane 502a to raster plane 502b. There may be any number of intermediate positions.

When the scanning X-ray source 501 is in position 506 of raster plane 502a, ray 522 travels from position 506 through a portion of the specimen S, and is diffracted from region 510. Region 510 is within sensed-volume 519. The sensed volume 519 and the diffracted ray path 520 are defined by the geometry of collimator 504. Thus, detector 503 preferentially detects diffracted X rays emanating from within the sensed volume 519. Region 509, within sensed volume 519 also diffracts ray 523 from source position 506 along path 520 that are detected by detector 503. However, it is possible that the crystalline lattice spacing, "d", in separate regions of sample 5 is such that the diffracted rays from both region 509 and region 510 are of the same wavelength and are, thus, indistinguishable to the detector 503 if the X-ray source 501 remains within the raster plane 502a.

If the X-ray source 501 is moved to raster plane 502b, source position 507 produces a diffraction ray from region 510 along path 520. However, region 509 does not produce a diffraction ray along path 520 when the source is in position 507. This is governed by the physical characteristics of the specimen and the interaction of the X rays with the specimen's atomic structure, known in the art. For region 509 to diffract along path 520, the source must move to position 508 in raster plane 502b. Diffracted X rays from the two regions are no longer indistinguishable by detector 503. Source position 506 produces ray 522 and ray 523. Source position 507 produces ray 522 and ray 505 but cannot produce ray 523. Source positions 506 and 507 define ray 522. The intersection of ray 522 and path 520 identifies region 510 and distinguishes it from region 509, and every other region within the specimen S.

With reference to FIG. 5 detector 517 and collimator 516 define diffraction path 521 and sensed volume 518. Sensed volume 518 is distinct from sensed volume 519, with the exception of a small common volume 526 roughly at region 510. At source position 513 in raster plane 502b, ray 524 is diffracted in region 511 along path 521. Source position 513 also produces ray 525 that diffracts in region 512 and produces a diffracted ray along path 521. It is possible that the crystalline lattice spacing, "d", in separate regions of the specimen is such that the diffracted rays from both region 511 and region 512 are of the same wavelength and are thus indistinguishable if the source remains within the raster plane 502b. These two, separate, diffraction sites might be indistinguishable to detector 517 if only a two-dimensional source scan were used.

If signals are gathered, subsequently, using a different raster plane 502a, then ray 524 would be produced from source location 515, and ray 525 would not be produced by source location 515, but by source location 514. Thus, similarly to the previous example, diffraction from regions 511 and 512 can be distinguished if the X-ray source is scanned in three dimensions.

When processing the data from a three-dimensional X-ray source scan, the goal is to section the specimen into small, separate, volumes and to extract XRD information about each individual volume.

FIG. 6 is a flowchart showing the invention perform a texture measurement. A texture map is a visual representation or image of an orientation distribution function (ODF). One selects a specific specimen crystalline axis, say 100, which has a specific "d" spacing, and plots the distribution of this orientation on a sphere. The fraction of the total volume of the material with a specific crystalline orientation determines how intense a "dot" is plotted at the point corresponding to that specific orientation. If there is no preferred orientation, the ODF would be a uniformly gray sphere. If, however, a preferred orientation is present, the surface of the sphere would appear mottled or spotted. For example, a single crystal would produce an OFD with only a few, intense, symmetric, pin-points on the surface.

A measurement of texture (anisotropic crystalline orientation) can be very rapidly made with the present invention. Given the location and orientation of the detector collimator, the location of the specimen and the location of the scanning X-ray source, it is easy to calculate the incident and diffracted beam angles. A computer CPU is used to control the scanning X-ray source position. Typically a raster scan is implemented. The same computer CPU controls a single-channel analyzer (SCA). Although the function of the SCA is well-known in the art, its basic operation is explained herein. The detector produces an electronic pulse each time an X-ray photon enters its sensitive region (volume). The height of this pulse is proportional to the energy that the x-ray photon has deposited in the detector volume. The height of each pulse is, thus, inversely proportional to the wavelength of the X-ray photon that produced the pulse. The SCA only allows pulses of a selected height range to pass. The range of heights can be controlled via an electronic signal or via manual controls on the SCA itself. The pulses leaving the SCA are counted by the computer. The number of counts at a given position (pixel) per unit time is directly related to the intensity for the corresponding pixel in an image that the computer will form on a CRT display. Assuming the computer CPU holds the programming signal to the SCA constant, the image that appears on the CRT will be one of a single X-ray wavelength. In the case of a texture map, however, an image produced from a constant "d" (crystalline lattice spacing) is desired. This selects a specific crystalline axis. Therefore, the computer is programmed to alter the signal to the SCA to hold a constant "d". This is done by using the Bragg equation. The calculated θ and the selected "d" are inserted into the Bragg equation. The resultant λ is used to set the programming signal to the SCA.

Referring again to FIG. 6, the texture measurement flowchart, the first step, 601, is to input the values for d, Jsize, Ksize, and X. Steps 602 and 603 iterate through the two-dimensional source scan. The next step is to move the source to the required position in the raster plane. The procedure RasterTo( ) step 603, causes the X-ray source to actually move via electronic signals from the computer CPU to the motion-control hardware. A neutron or gamma ray radiation source could be used in addition to an X-ray source. The x, y, and z coordinates of source position J, K are placed in the variables Xr, Yr, and Zr in step 605. In step 606, the coordinates of the centroid of the sensed volume are placed by the CPU in the variables Xc, Yc, and Zc. In step 607 the CPU calculates the distance R between the source and the centroid of the sensed volume within the specimen. The variable Xr contains the X coordinate of the source within the raster plane. The variable Xc contains the X coordinate of the centroid of the sensed volume. In a like fashion, the variables Yc and Zc contain the Y and Z coordinates of the centroid of the specimen and the variables Yr and Zr contain the Y and Z coordinates of the source position. The Z axis of the rectilinear coordinate system is assumed to be parallel to the axis of the collimator. This is for ease of calculation. Any coordinate system could be used, but the transformations and calculations would tend to reduce the clarity of the presentation.

Next, in step 608, the angle 2θ is calculated. Referring to FIG. 3, 2θ is shown to be the angle formed between the projection of the ray 302 from the source 301 as it emerges from the specimen 303, and the path of the diffracted X ray 312. Path 312 is also referred to as the collimator path. The operator adjusts the invention to make it sensitive to a specific "d". Thus, the CPU must adjust λ, using the SCA, at each source position. Referring back to FIG. 6, the rotation angle y about the collimator path is then calculated in step 609. This angle λ, along with the angle θ are used to determine the coordinates, on the imaginary unit radius sphere representing the ODF, to which this data point is to be assigned. The angles λ and 2θ, are likewise the coordinates on the imaginary sphere representing reciprocal space. In step 610 the Bragg equation is used to calculate the needed λ. The value n in the Bragg equation is assumed to be 1. Once a new λ is calculated, in step 611 adjustment of λ is performed via the SCA programming signal. In step 612 the photon counter is then reset. Only pulses corresponding to the correct λ pass through the SCA and are counted by the counter. The computer CPU is then gathering only the data relevant to a selected crystalline axis. In step 613, the computer now waits for a set time X. This time is set by an operator before the measurement starts. The time X must be long enough so that there are more than just a few photon counts in each detector position, but short enough so that the total time for the measurement is not overly long. Next, in step 614, the computer reads the counter. The number of pulses per unit time corresponds to the X-ray intensity.

The diffracted X-ray intensity is affected by the radiation source-to-specimen distance. To correct for this, the counter reading Counts must be multiplied by $R^2$ to give Better-Counts. This is accomplished in step 611. This correction must be made to the measured intensity because the X-ray intensity varies inversely with distance. Since the radiation source-to-specimen distance varies as the source scans, it is important to make this correction. Since the intensity of the X-ray source is not uniform over its spectrum, the data gathered must be scaled, using knowledge of the X-ray source intensity as a function of wavelength. In step 615, BetterCounts is scaled by the reciprocal of the function SourceSpectrum(λ) to give the function EvenBetterCounts. The function SourceSpectrum(λ), in step 616 returns the source intensity, in counts per second, at a given wavelength and at a set distance from the source. The data used to develop this function is measured during or before the XRD measurement process being described. It is well known in the art that it is important to correct the relative intensity of each piece of XRD data gathered with respect to other XRD data in the same measurement set. This allows more meaningful analysis of XRD data gathered.

The final two steps of the process is to plot the XRD data points in the correct spot on the surface of the imaginary sphere in reciprocal space in the step 617 and on the correct spot on the ODF in step 618. The data structures ODF and Recip represent imaginary unit radius spheres. The data structures ODF and Recip would typically be viewed and evaluated using a 3-D rendering package such as Axum※ or PV Wave※. The structure ODF contains a orientation distribution function that represents the texture of the material within the sensed volume. The structure Recip contains the same information, but in reciprocal space.

For many applications the reciprocal space representation of the texture map would suffice. Since there is a point-to-point correspondence between the source position and the positions on the ODF and the reciprocal space ODF, a pixel reassignment map need be calculated only once (if desired) for a given specimen-collimator-source plane geometry. The SCA setting may also be pre-calculated for each source position and stored in a table, if so desired. Thus, a real-time ODF may be easily displayed with a bare minimum of real-time calculation.

Steps 620 and 621 close the iteration loops J and K that run until Jsize and Ksize are reached. The radiation source scan possesses Jsize times Ksize pixels.

FIG. 7 is the single wavelength flowchart showing the invention as used to perform chemical analysis. A popular use of XRD is chemical analysis. In the realm of XRD this is known as "phase" identification. Every crystalline chemical species has a unique set of atomic spacings. The arrangement of the atoms within the molecule and the arrangement of the molecules within the crystal is what determines this atomic spacing and is also what makes the chemical phase" unique. These "d" spacings are easily measured using XRD.

In a traditional powder diffractometer, wavelength (λ) is held fixed and sin θ is incrementally varied. The powdered specimen diffracts more and less intensely as sin θ is varied.

The intensity is plotted versus sin θ (or "d".) This plot is often called a diffraction "trace." The trace is representative to the atomic spacings present in the powder. The trace is compared by an operator to the traces of known substances. Once a trace match is made, the substance is identified.

The moving-source XRD method disclosed herein may be easily used for phase identification. Unlike prior methods, a powder need not be prepared to obtain a quality analysis using the present invention. This is because the XRD data is gathered in a two-dimensional scan instead of just a one-dimensional scan of the prior art. Thus, there is no need to reduce the dimensionality of the problem artificially by preparing a randomly oriented powder. Random crystallite orientation is not needed if a two-dimensional scan is performed. Since nearly all objects have non-random crystallite orientation, phase identification analysis can be performed on all types of objects, non-destructively, in their native state, using this invention.

For example:

The single-wavelength method may be used. The physical set-up of the invention is very similar to that used in the above "texture measurement." The collimator is aimed at the specimen. An SCA is used. The output of the SCA is collected by the computer. The programming signal for the SCA is set to a given wavelength either manually or by the computer. The data gathered will thus be for a single wavelength.

Referring again to FIG. 7, the phase identification flowchart, shows how the instrument is operated and how the data is processed to do phase analysis at a single wavelength using an SCA. In step 701 values for Jsize, Ksize, X, and Max_d are input. In step 702 the user sets the SCA to the desired wavelength, λ, either manually via the knob on the SCA or via an electronic programming signal from the computer. In steps 703, 704, 705, and 706 the variables used by the CPU program to hold the trace information are then initialized.

Steps 707 and 708 iterate though the source scan. Next, in step 709 the X-ray source is moved to a specific raster position via procedure RasterTo(J,K). The procedure RasterTo(J,K) causes the radiation source to actually move via electronic signals from the CPU to the motion control hardware. The x,y, and z coordinates of source position J,K are placed in the variables Xr, Yr, and Zr in step 710. In step 711, the coordinates of the centroid of the sensed volume are placed by the CPU in the variables Xc, Yc, and Zc. In step 712 the CPU calculates the distance R between the source and the centroid of the sensed volume within the specimen. The variable Xr contains the X coordinate of the source within the raster plane. The variable Xc contains the X coordinate of the centroid of the sensed volume. In a like fashion, the variables Yc and Zc contain the Y and Z coordinates of the centroid of the specimen and the variables Yr and Zr contain the Y and Z coordinates of the source position. The CPU calculates angle 2θ in step 713. The Z axis of the rectilinear coordinate system in this example is assumed to be parallel to the collimator axis. The photon counter associated with the SCA is then reset to zero in step 714. After a wait of X milliseconds, step 715, the photon counter is read by the CPU, step 716. The actual wait time is best determined by trial and error by an operator. One wishes to acquire a reasonable number of events at each position, but this is balanced against the need to make the total measurement in a timely manner.

At step 717 the CPU calculates the "d" spacing for the specimen under examination. In step 718, the CPU scales the number of photon counts Counts by the factor $R^2$ to adjust for the variation in intensity caused by variation in specimen-to-source distance. This corrected value is stored in BetterCounts. BetterCounts is then summed into the proper element of dTrace in step 719. The corresponding counter to that element, dTraceCounter(d) is then incremented in step 720. Steps 721 and 722 close the iteration loops.

After the invention has completed the raster scan and has summed in the count at each position, the CPU steps through the array dTrace via step 722 and divides each element by the number of times it has added counts, dTraceCounter(I). In step 723 the CPU calculates an average within each element of dTrace. Step 724 closes the iteration loop on I.

The data held in dTrace is now in a format that can easily be processed with the standard trace-matching software (well known in the art, for example Jade™) that is used to process the data obtained with a traditional powder diffractometer.

The multi-wavelength method of phase analysis using moving-source XRD is an extension of the single-wavelength method. The single-wavelength method needs only an SCA. If a multi-channel analyzer (MCA) is used instead, data can be gathered at many wavelengths simultaneously. MCAs are well know in the art, but a brief explanation of the technology is given here for clarity. MCAs often have 8,000 wavelength channels or more. The electronic pulse caused by each x-ray photon that is detected is then sorted and placed in a separate data "bin" by the MCA. Each bin holds the number of photons of a specific, very narrow range, of wavelengths. The MCA memory is reset as the moving source moves to a new position range. Sorting and counting commences and continues while the source dwells in a specific "pixel". Just as the source leaves a pixel, the MCA bin memory is copied. As the source moves into the next pixel region, the MCA memory is reset and the counting process begins again.

Referring to FIG. 8, the multi-wavelength chemical analysis flowchart, shows the sequence of events in this process. First, in step 801 the variables Jsize, Ksize, Max_d and X are inputted. Steps 802, 803, 804, and 805 initialize the variables dTrace and dTraceCounter. Steps 805 and 807 iterate through the radiation source positions. The radiation source is then moved to a specific position in the raster plane in step 808. The procedure RasterTo(J,K) causes the radiation source to actually move via electronic signals from the CPU to the motion control hardware. The x,y, and z coordinates of source position J,K are placed in the variables Xr, Yr, and Zr in step 809. In step 810, the coordinates of the centroid of the sensed volume are placed by the CPU in the variables Xc, Yc, and Zc. In step 811 the CPU calculates the distance R between the source and the centroid of the sensed volume within the specimen. In this case, the Z axis of the rectilinear coordinate system is parallel to the collimator axis. This is done in the interest of clarity and simplicity. The diffraction angle 2θ is then calculated by the CPU, using standard trigonometric techniques, in step 812.

The MCA bin memory is then reset in step 813. Next, the MCA is commanded by the CPU to start taking data in step 814. The CPU waits for a specific period of time for photon counts to accumulate in the bins in step 815. This time is set by trial and error by an operator. The goal is to wait long enough for more than just a few photon counts to accumulate in each bin, but not wait so long that the total measurement process is overly long. When time X has expired, in step 816, the CPU stops the MCA and then processes the data in the bins.

Each MCA bin is processed separately. Step 817 increments through each bin of the MCA. In step 818, the number of photons that were sorted into bin #I is moved into the variable Counts. The calibration data for the MCA is used to assign a wavelength λ to each of the numbered bins in step 819. In FIG. 8, the function MCAbinLambda( ) performs this task. Since the intensity of the X-ray source is not uniform over its spectrum, the data gathered must be scaled, using knowledge of the X-ray source intensity as a function of wavelength. In step 820, Counts is scaled by the reciprocal of the function SourceSpectrum(λ) to give the value BetterCounts. The function SourceSpectrum(λ), in step 820 returns the source intensity, in counts per second, at a given wavelength and at a set distance from the source. The data used to develop this function is measured during or before the XRD measurement process being described. It is well known in the art that it is important to correct the relative intensity of each piece of XRD data gathered with respect to other XRD data in the same measurement set. This allows more meaningful analysis of XRD data gathered. In step 820 the value in BetterCounts has thus been corrected for variations in intensity of the source spectrum. Next, in step 821, the factor $R^2$ is used to correct for the change in intensity caused by variation in the distance between the source and the specimen. This fully-corrected value is stored in EvenBetterCounts.

The CPU now calculates "d" using the Bragg equation to select the correct element in dTrace to place the latest data in step 822. EvenBetterCounts is summed into the correct element of dTrace, step 823. The variable EvenBetterCounts is fully corrected for both spectrum and distance variations in intensity. The counter, dTraceCounter(d), corresponding to the selected element is then incremented in step 824. Steps 825, 826 and 827 close the iteration loops L, K, and J.

After performing this process on all Lmax bins for all the (Jsize×Ksize) raster locations, the CPU continues with the data reduction process. In steps 827, 828 and 829, each element of the array dTrace is divided by its corresponding counter, dTraceCounter(I). Thus, each element of dTrace now contains the average of all the data placed in it during the raster scan. The data held in dTrace is now in a format that can easily be processed with the standard tracematching software such as Jade™ that is used to process the data obtained with a traditional powder diffractometer.

If the MCA used has 8,000 channels, the phase analysis measurement can be performed about 8,000 times faster than would be using an SCA and the single wavelength method. If desired, the measurement time can remain the same as the single-wavelength method, but the source intensity, and thus the x-ray exposure for the specimen, can be reduced by a factor of 8,000.

In addition to exposure/speed advantages, a greater range of "d" spacings can be gathered using the same solid angle of source movement. This is because information is gathered over a greater range of wavelengths.

As described above, there is a "sensed volume" of the specimen. This sensed volume is defined by the solid angle of the collimator as it intersects the specimen. It is actually a very tall and narrow cone but it may be described roughly as a thin cylindrical volume within the specimen. In the above examples, the XRD analysis is performed on the entire sensed volume. The analytical result is an "average" of the measured characteristics of all the material contained in the sensed volume.

Computed tomography techniques can be applied to effectively "slice" the sensed volume into many segments. There are many ways of gathering the additional data to extract depth information. In back-reflection mode, the detector and the source are on the same side of the specimen, the X rays that are diffracted deep within the specimen must penetrate more of the specimen material than those X rays that are diffracted close to the surface. Long-wavelength X rays are attenuated more severely than short-wavelength X rays as they travel though the specimen. One can compare the attenuation of first-order (n=1) diffracted X rays with the attenuation of higher-order diffracted X rays to determine the depth of the crystallite that produced the diffraction. Using the differences of attenuation at different wavelengths to determine thickness or depth is well known in the art.

One the methods that can be used to extract depth information is to scan the source in three dimensions rather than just two dimensions. Physically moving a planar, raster-scanned X-ray source accomplishes this goal. The simplest way to physically move the planar raster-scanned X-ray source would be to move such source in a plane perpendicular to the raster-scan plane. Multiple raster-scans would be used to build a three-dimensional array of X-ray source positions. The data gathered by each detector during this 3-D X-ray source scan can be manipulated by CT techniques to effectively partition the sensed volume into many small segments.

For example:

Assume a single crystallite within the sensed volume. This crystallite diffracts an X ray of wavelength λ when the source is in raster position X0, Y0. If the "d" spacing is unknown, it is not possible to exactly calculate the position of the crystallite within the sensed volume. If we physically move the raster plane in the Z direction from our initial Z0 to a new position Z1, the observed diffraction no longer occurs at raster coordinates X0, Y0. It will now occur at X1, Y1. The two sets of X, Y, and Z coordinates fully define the primary beam vector. This is because two points define a line. The intersection of the primary beam with the diffracted beam (defined by the collimator position and orientation) uniquely define the three-dimensional coordinates of the diffracting crystallite. This is because the intersection of two lines defines a point.

In reality, there will be a multiplicity of crystallites and a multiplicity of primary bean vectors and diffracted beam vectors each contributing to the diffraction data gathered during the 3-D X-ray source scan. CT algorithms, well-known in the art, can be used to converge on the solution to the resultant large system of simultaneous equations. The solution, in this case, will be the assignment of diffractors (i.e. crystallites) to specific segment locations within the sensed volume cylinder.

FIG. 9 is a flowchart which illustrates the computed tomography process. Steps 902 through 903 get input from the operator. Steps 904 though 917 acquire XRD data. Steps 918 through 951 process the acquired XRD data to extract information specific to each segment along the axis of the sensed volume conic section.

In step 902, the number of pixels in each dimension of the radiation source scan is input to the CPU. These values are stored in memory as Isize, Jsize, and Ksize. Also in step 902, the photon acquisition time, X, is input by the operator. The number of segments that the operator wishes the sensed volume to be "sliced" into is input and stored in the variable NumberOfSegments in step 903.

Steps 905, 906, 907 are the for-loop commands to the CPU to iterate through the three-dimensional radiation, X-ray, source scan. I, J, and K represent each of the three dimensions. In step 907, the radiation source is moved by the CPU via electronic signals to the motion control hardware. Thus, the radiation source is moved to the x,y,z coordinates that correspond to the I,K,J pixel. When the move is complete, step 908 resets the MCA memory, readying the system to take spectral data. The MCA photon acquisition process is started in step 909. Step 910 is a wait by the CPU of X milliseconds for photon counts to accumulate in the MCA bins. The actual wait time is best determined by trial and error. One wishes to acquire a reasonable number of events at each position, but this is balanced against the need to make the total measurement in a timely manner. After the wait, the CPU at step 911 stops the MCA data acquisition process. The contents of the bin memory held in MCAbinmemory is transferred to a structure PixelSpectrum(I,K,J) in step 912. The structure PixelSpectrum is a three-dimensional array of bin memories. This process is repeated for each pixel in the three-dimensional radiation source scan via steps 913,914 and 915.

At step 916 the CPU iterates through each of the NumberofSegments into which the sensed volume is to be sliced into. This step selects the Lth segment of the sensed volume. In steps 917 through 922 the CPU initializes data structures Sspectrum and Scount. These data structures will hold intermediate results of the tomography process. Sspectrum represents a unit radius imaginary sphere. Scount tracks the number of times that spectral information has been summed into each specific element of Sspectrum. Steps 923,924, and 925 sequence though the extent of the values of I, J and K. The x,y, and z coordinates of pixel I,J,K are placed in the variables Xs,Ys, and Zs in step 926. In step 927, the coordinates of the centroid of the Lth segment of the sensed volume are placed by the CPU in the variables Xc,Yc, and Zc. The CPU then calculates the path distance Rp, between the centroid of the Lth segment and the J,K,Lth pixel in step 928. The angle 2θ between the path along distance Rp and the collimator path is calculated in step 929. The axis of the imaginary sphere represented by Sspectrum is chosen to be the axis of the collimator path. The CPU calculates the rotation angle λ in step 930.

The CPU then scales the spectrum data in element PixelSpectrum(I,J,K,) by the factor $Rp^2$ in step 931. In the next step, 932 the CPU sums the scaled spectrum, into the spectrum structure of Sspectrum(φ,λ). The Scount that is associated with spectrum in Sspectrum(φ,λ) is incremented in step 933. Every pixel in the structure PixelSpectrum is processed in this manner once via steps 934,935, and 936. In Steps 937,938,939,940, and 941 the CPU calculates the average within each element of spectrum. After this averaging process is complete, step 942 stores the structure Spectrum in the Lth element of the structure SegmentXRDpattern. This process is repeated via step 943 for each element of the data structure NumberofSegments.

Each pixel array within data structure SegmentXRDpattern now contains XRD data that is very strongly associated with individual segment volumes and only very weakly influenced by the remainder of the sensed volume. A simple average was used to process the pixels along a single projection line of a single virtual projection sphere. Much more sophisticated processing algorithms are known in the art.

Each pixel array (element) within data structure SegmentXRDpattern is a "color" Laue pattern defined by in spherical coordinates. The XRD data contained within each element can be easily processed for chemical phase analysis, texture analysis, or it may be simply presented as a color Laue pattern. All the XRD information is present to do any type of XRD analysis required.

The previous text illustrates transformation of the raw XRD data from rectilinear coordinates to spherical coordinates, making the intensity correction ($R^2$) associated with the transform and processing the data in spherical coordinates as needed to obtain texture information or chemical phase information. The data in each element of SegmentXRDpattern is already in spherical coordinates and the $R^2$ intensity corrections have been made. It is a simple matter for anyone skilled in the art to complete the processing of the data in a manner very much like that shown above, and to extract XRD information such as the texture ODF or the diffraction trace.

FIG. 10 shows the process for extracting texture information from the data structure SegmentXRDpattern. Step 1001 allows the operator to select a "d" spacing for the texture map. Step 1002 sequences through each of the NumberOfSegments contained in the data structure SegmentXRDpattern. Step 1003 selects the Lth element of Sspectrum from SegmentXRDpattern. Steps 1004 and 1005 initialize structures ODP and Recip to null values.

Steps 1006 and 1007 sequence through the extent of values for 2θ and λ corresponding to the elements of Sspectrum. Step 1008 retrieves a spectrum from Sspectrum and places it in the array BinSet. Next, in step 1009, the CPU uses the Bragg equation to calculate the wavelength λ. It is assumed that "n" in the Bragg equation is equal to one. In step 1010, the CPU selects the bin that holds the portion of the spectrum that includes λ. The CPU does this using the MCA calibration data. Step 1011 transfers the contents of the selected bin to the variable Counts. In step 1012, the CPU corrects for source spectrum variation. The function SourceSpectrum(λ), returns the source intensity, in counts per second, at a given wavelength and at a set distance from the source. The data used to develop this function is measured during or before the XRD measurement process being described. It is well known in the art that it is important to correct the relative intensity of each piece of XRD data gathered with respect to other XRD data in the same measurement set. This allows more meaningful analysis of XRD data gathered. Thus, value in BetterCounts has thus been corrected for variations in intensity of the source spectrum.

Now that the intensity data point has been fully corrected, in step 1013 it is transferred into the proper element of a data structure Recip. Next, in step 1014 the value in BetterCounts is transferred to the proper element of the structure ODF. In step 1015, the value in BetterCounts is copied to the symmetric element in the structure ODF. Step 1016 closes the iteration loop on variable λ. Step 1017 likewise closes the loop on the variable 2θ. Step 1018 copies the fully processed result Recip into the Lth element of an array of like structures. Step 1019 performs a like operation on the structure ODF. Step 1020 closes the iteration loop on the variable L.

The result of this process is two arrays of unit sphere data structures. The structures within the array ODF_Array are orientation distribution functions, representative of the texture of the material in the Lth segment of the sensed volume. RecipArray likewise holds structures containing the same information, but representing the data in reciprocal space instead. The data structures ODF and Recip represent imaginary unit radius spheres. The data structures ODF and Recip would typically be viewed and evaluated using a 3-D rendering package such as Axum or PV Wave.

FIG. 11 shows how the data contained in structure SegmentXRDpattern can be processed to obtain phase identification information. Step 1101 sequences through each of the NumberOfSegments elements in the data structure SegmentXRDpattern. In step 1102, the CPU retrieves the Lth element from SegmentXRDpattern and places the data in Spectrum. Sspectrum now holds the XDR data associated with the Lth segment of the sensed volume in the format of a unit radius sphere. Next, in steps 1103,1104,1105, and 1106, the CPU initializes the arrays dTrace and dTraceCounter.

Steps 1107 and 1108 sequence through the range of elements in Sspectrum. The element Sspectrum(2θ, λ) is copied to the array BinSet in step 1109. BinSet now holds the spectrum at point 2θ, λ on the unit radius sphere. Step 1110 sequences through each element of BinSet. The Ith element of BinSet is retrieved by the CPU in step 1111 and placed into the variable Counts. Next the center wavelength of the Ith element is calculated in step 1112. This is done using the calibration data for the MCA. Step 1113 corrects for variation in the source intensity. Function SourceSpectrum(λ) returns the intensity of the source in counts per second, for a given wavelength λ, at a set distance. The spectral data used to produce this function can be measured before or during the present scan.

Next, in step 1114, we calculate the "d" spacing using the Bragg Equation. We assume n, in the Bragg equation, is equal to one. In step 1115, the CPU selects the element in the array dTrace that corresponds most closely with the "d" spacing calculated previously. The CPU then sums in the corrected intensity BetterCounts. Step 1116 increments the counter, dTraceCounter(d) associated with dTrace(d). Step 1117 closes the I iteration loop. Step 1118 closes the λ iteration loop. Step 1119 closes the 2θ iteration loop.

Steps 1120,1121, and 1122 take the average within each element of the array dTrace. Now that the diffraction data is completely processed in the array dTrace, the array is copied to the Lth element of the data structure dTraceArray in step 1122. Step 1124 closes the iteration loop for L.

Each element of dTraceArray holds a diffraction trace, intensity vs. "d" spacing, that is strongly associated with the Lth segment of the sensed volume. This diffraction trace may be easily processed for phase identification using standard pattern-matching software, known in the art, such as Jade™.

With the ability to recover depth information available, it is readily apparent that the XRD properties of any single portion of the entire volume of an object can be measured. By multiple measurements of this type, the entire volume of an object can be broken up in to small "compartments." XRD measurements can be made on each individual compartment.

Multiple measurements as needed can be obtained by many means including; raster-scanning the specimen, raster-scanning the detector with its collimator across the specimen, or by using multiple detectors and collimators FIG. 12 shows a scanning source 1201 of X rays with a typical raster pattern 1202. This technique allows 3-D inspection of objects in terms of texture, chemical composition, mechanical strain, temperature, and other material properties that can be sensed using XRD. The material properties that can be sensed using XRD are well-known in the art.

For clarity of presentation, FIGS. 6, 7, 8, 9, 10 and 11 show the CPU in control of XRD system timing and radiation source position sequencing. These tasks can easily be performed by the motion control system instead. Thus, instead of the CPU commanding the motion control system to move the source to a given position, the motion control system can, itself, determine the source position sequence and inform the CPU when the source has reached each successive position. As long as the CPU and the motion control share source position information, either system may serve to select the sequence of radiation source positions and command the motion.

Simultaneous XRD Measurement and Radiography using the Moving Source Method

Radiographic and XRD measurements can often be complimentary. As noted in this text, each provides different information about the object being inspected. For example a simultaneous radiograph would be useful to document or ascertain the location of the specimen during XRD measurements. Physical positions, and features could be directly associated with XRD measurements.

It is relatively easy to make radiographs simultaneously as one makes XRD measurements using the moving source method. Albert '229, referenced in the prior art, describes the use of a moving source and fixed detector to generate radiographs. If an uncollimated detector is placed as described in the reference, a radiograph will result. A collimator could be used on the radiographic detector, but it would be fashioned to accept primary rays and to reject secondary rays. This radiograph may be obtained in parallel with XRD measurements being made using the same source, but using different collimators of a different design than those used for XRD measurements (if any), different detectors, and different data analysis.

Typically, for reverse-geometry radiographic imaging, the specimen (object) is placed close to the raster plane. The detector is held somewhat distant to the specimen. For XRD measurements, however, the specimen is generally placed distant from the raster plane and close to the collimator/detector. For simultaneous XRD and radiography, some compromise in the positioning of the elements must be made. Often, the XRD collimator and detector is placed between the specimen and the radiographic detector. Thus, the collimator and detector (being used for transmission XRD measurements) can partially block the view of specimen by the radiographic detector. Reflection mode XRD collimators and detectors are not always placed such that they would be visible in the radiograph. However, the specimen is placed in a less than ideal position, relative to the raster plane, for radiographic imaging, during XRD measurements. This is especially true for reflection mode XRD measurements.

FIG. 13 depicts the relative spacing of the specimen S1, S2 for a radiographic measurement versus diffraction measurement. For example a human breast specimen S1, the distance R2 between the specimen S1 and the source X in radiography is relatively small (nominally 0.25 inch) as compared to the distance R1 (nominally 6–36 inchs) between the collimator/detector and the specimen. On the other hand the distance R10 between the specimen S and the source in diffraction, is relatively small (nonimally 0.5 inch) as compared to the distance R20 (nominally 24 inches) between the source and the specimen S2. R30 is nominally 0.5 inch or less. Thus, the two methods differ greatly as to the relative spacings used.

Although the present invention has been described with reference to preferred embodiments, numerous modifications and variations can be made and still the result will come within the scope of the invention. No limitation with respect to the specific embodiments disclosed herein is intended or should be inferred.

While in the foregoing, embodiments of the present invention have been set forth in considerable detail for the purposes of making a complete disclosure of the invention, it may be apparent to those of skill in the art that numerous changes may be made in such detail without departing from the spirit and principles of the invention.

INFORMATION DISCLOSURE STATEMENT

U.S. Pat. No. 5,684,857 (1997) to De Bokx discloses a method for GE-XRF X-ray analysis of materials and apparatus for carrying out the method. FIG. 1 shows an X-ray source 4, a front collimator 14, specimen 16, back collimator 18, and detector 20.

U.S. Pat. No. 5,481,109 (1996) to Ninomiya et al. discloses a surface analysis method and apparatus for carrying out the same (see FIGS. 1, 7–16).

U.S. Pat. No. 5,457,727 (1995) to Frijlink discloses a device for processing a measured signal corresponding to the intensity of X-rays reflected by a multi-layer structure on a substrate. FIG. 7 shows an X-ray source 1, a collimator system 2 and 3, a goniometer specimen support 9, a collimator system 5, and a detector 8.

U.S. Pat. No. 5,384,817 (1995) to Crowther et al. discloses an X-ray optical element and method for its manufacture. FIG. 1 shows an X-ray optical element and method for its manufacture. FIG. 1 shows an X-ray source 12, a sample 16, a device 20 (which can be a collimator), a reflective element 22 and a detector 24. This figure is analogous to the typical arrangement as shown the attached FIG. 1.

U.S. Pat. No. 5,267,296 (1993) to Albert discloses X-ray images produced on a monitor display screen by situating the subject between a detector having a minute X-ray-sensitive area and an x-ray source having an extensive anode plate on which an X-ray origin point is swept in a raster pattern similar to the raster of the display monitor.

U.S. Pat. No. 5,263,075 (1993) to McGann et al. discloses a high-annular resolution X-ray collimator. FIGS. 1–2 show an X-ray source 10, a slit collimator 20, and detectors 32.

U.S. Pat. No. 5,008,910 (1991) to Van Egeraat discloses an X-ray analysis apparatus comprising a sagittally curved analysis crystal. FIG. 1 of Van Egeraat shows a laser source 2, a specimen 6, an analysis crystal 8, a collimator 18, and a detector 16. This figure shows similar arrangement as shown in the attached FIG. 2.

U.S. Pat. No. 4,104,519 (1978) to Oldendorf discloses a method and apparatus for retrieval of exposure information from film images. FIG. 5 shows a raster derive circuit 20, a source 12, a collimator 14, a filter 32, a film 16, and detector 26.

U.S. Pat. No. 3,949,229 (1976) to Albert discloses radiographic images of high definition and clarity produced quickly and with reduced radiation exposure of the subject by utilizing a scanning X-ray source in which a moving point source of x-rays is created by sweeping an electron beam in a raster pattern on a broad anode.

U.S. Pat. No. 3,885,153 (1975) to Schoeborn et al. discloses a multi-layer monochromator. FIG. 2 shows two annular slits to produce a collimated neutron beam 13, a monochromator crystal 11, and a detector 15.

U.S. Pat. No. 3,373,286 (1968) to Han discloses a device for measuring the characteristics of a material moving on a conveyor with means for minimizing the effect of flutter. FIG. 1 shows a radiation source 2, a material 3, (which can be made of metal, plastic, etc. Column 3, lines 55–60), a collimator 12 and a detector 4. This patent shows similar arrangement as required in the reverse geometry embodiment of the attached FIG. 2.

What is claimed is:

1. A scanning X-ray diffraction system for X-ray diffraction measurements comprising:
   a. an X-ray source;
   b. means for sweeping said X-ray source in a predetermined multi-dimensional pattern to emit X rays successively from different positions relative to a specimen, and to vary the Bragg angle between X rays transmitted to and diffracted by the specimen;
   c. an X-ray detector spaced apart from said X-ray source to receive said X rays transmitted to and diffracted by the specimen, said X-ray detector having a radiation sensitive region and having means for producing an electrical output signal indicative of said diffracted X rays impinging on said radiation sensitive region of said detector; and
   d. an X-ray collimator disposed between the specimen and said detector, said X-ray collimator directing X rays diffracted by the specimen to said X-ray detector.

2. The scanning X-ray diffraction system as in claim 1, wherein said collimator is adjacent to said detector and in alignment with said detector to cause said detector to receive diffracted radiation from the specimen.

3. The X-ray scanning system as in claim 2, wherein said means for sweeping said X-ray source further comprises processing means for correlating the position of the x-ray source with a detector ouput signal.

4. The X-ray scanning system as in claim 3 wherein said processing means further comprises a single channel analyzer whereby the signal pulses of said electric output signal are counted.

5. The X-ray scanning system as in claim 3 wherein said processing means further comprises a multiple channel analyzer whereby each of said electric output signals is sorted by wavelength.

6. The X-ray scanning system as in claim 4, wherein said system further comprises a display having a raster pattern synchronized with that of said means for sweeping said X-ray source and having an intensity control responsive to said processor means.

7. The scanning X-ray diffraction system as in claim 6, wherein said detector is movable to any position on a spherical geometry, said spherical geometry having a specimen at its center; and
   said collimator having an axis aligned along a radius from said detector.

8. The scanning X-ray diffraction system as in claim 7 wherein an axis of said collimator is movable to any radial position relative to said detector, whereby said detector receives diffracted radiation from each selected position.

9. The X-ray scanning system as in claim 5, wherein said system further comprises a display having a raster pattern synchronized with that of said means for sweeping said X-ray source and having an intensity control responsive to said processor means.

10. The scanning X-ray diffraction system as in claim 9, wherein said detector is movable to any position on a spherical geometry, said spherical geometry having a specimen at its center; and
    said collimator having an axis aligned along a radius from said detector.

11. The scanning X-ray diffraction system as in claim 10 wherein an axis of said collimator is movable to any radial position relative to said detector, whereby said detector receives diffracted radiation from each selected position.

12. A scanning X-ray diffraction system for X-ray diffraction measurements comprising:

a. an X-ray source;
b. means for sweeping said X-ray source in a predetermined multi-dimensional pattern to emit X rays successively from different positions relative to a specimen and to vary the Bragg angle between X rays transmitted to and different by the specimen;
c. a plurality of X-ray detectors radially oriented about a specimen spaced apart from said X-ray source to receive X rays transmitted to and diffracted by a specimen, said X-ray detectors each having a radiation sensitive region and each having means for producing an electrical detector output signal indicative of X-rays collimators each disposed between a specimen and each of said X-ray detectors.

13. The scanning X-ray diffraction system as in claim 12, wherein each of said collimators is adjacent to a corresponding X-ray detector, each collimator having an axis in alignment with said corresponding X-ray detector thereby causing each X-ray detector to receive diffracted radiation from a specimen.

14. The X-ray scanning system as in claim 13, wherein said means for sweeping said X-ray source further comprises a processing means for synchronizing the position of the X-ray source with an electric ouput signal.

15. The X-ray scanning system as in claim 14, wherein said processing means further comprises a single channel analyzer whereby the signal pulses of said electric output signal are counted.

16. The X-ray scanning system as in claim 14, wherein said processing means further comprises a multiple channel analyzer whereby each of said detector output signals are sorted by wavelength.

17. The X-ray scanning system as in claim 15, wherein said system further comprises a display having a raster pattern synchronized with that of said means for sweeping said X-ray source and having an intensity control responsive to said processor means.

18. The scanning X-ray diffraction system as in claim 17, wherein each of said X-ray detectors is movable to any position on a spherical surface, said spherical surface having a specimen at a center and each of said collimators being aligned along a radius from said detector.

19. The scanning X-ray diffraction system as in claim 18, wherein each of said collimators is movable to any radial position relative to each of said X-ray detectors, whereby each detector receives diffracted radiation from a plurality of directions.

20. The X-ray scanning system as in claim 16, wherein said system further comprises a display having a raster pattern synchronized with that of said means for sweeping said X-ray source and having an intensity control responsive to said processor means.

21. The scanning X-ray diffraction system as in claim 20, wherein each of said X-ray detectors is movable to any position on a spherical surface, said spherical surface having a specimen at a center and each of said collimators being aligned along a radius from said detector.

22. The scanning X-ray diffraction system as in claim 21, wherein each of said collimators is movable to any radial position relative to each of said X-ray detectors, whereby each detector receives diffracted radiation from a plurality of directions.

23. A scanning x-ray diffraction (XRD) system for performing specimen texture analysis having a computer system having a memory, a display device, and a central processing unit (CPU) coupled to said memory, said CPU controlling the state of a plurality of processes for controlling the operation of the scanning X-ray diffraction system said XRD system comprising:
a. an X-ray source;
b. first processor means for sweeping said X-ray source in a predetermined multi-dimensional pattern;
c. second processor means causing said X-ray source to emit X rays successively from different locations in said predetermined pattern relative to a specimen;
d. at least one X-ray detector spaced apart from said X-ray source to receive X rays transmitted to and diffracted from a specimen, said detector having a radiation sensitive region and having means for producing an electrical output signal indicative of X rays impinging on said sensitive region of said detector;
e. an X-ray collimator disposed between a specimen and said detector causing diffracted radiation to be transmitted to a detector along a collimator path;
f. a memory for storing data files;
g. a CPU to receive said electrical output signal for processing, said processing comprising:
  correlating the position of said X-ray source to said detector electrical output signal;
  calculating a distance R between said X-ray source and the centroid of a sensed volume in a specimen;
  calculating an angle 2θ between said distance R and a collimator path;
  calculating a rotation angle y about said collimator path;
  calculating a wavelength X using the equation nλ=2d (sin θ);
  setting a signal to correspond to λ;
  resetting a photon counter, said photon counter responsive to said electrical output signals.

24. The system for controlling the operation of the scanning X-ray diffraction system as in claim 23, wherein said first processor means comprises a scanning X-ray source.

25. The system for controlling the operation of the scanning X-ray diffraction system as in claim 24, wherein said second processor means comprises a scanning X-ray source.

26. The system for controlling the operation of the scanning X-ray diffraction system as in claim 25, wherein said means to display comprises an input/output device; and
means to display data stored in said data files.

27. The scanning X-ray diffraction system for performing specimen texture analysis having a computer system having a memory, a display device, and a central processing unit (CPU) coupled to said memory, said CPU controlling the state of a plurality of processes for controlling the operation of the scanning X-ray diffraction system as in claim 23 comprising:
a. a mutiple channel analyzer(MCA) for processing said electric output signals, said MCA having a memory comprising a plurality of bins for storing said electronic output signals, said electronic output signals representing the wavelength, λ, of an X-ray;
b. said MCA connected to said CPU, said CPU sending and receiving signals from said MCA;
c. processing by said CPU of said electronic signals to create a data file in said memory of said CPU further comprising the steps of;
d. collecting said electronic output signals in each of said MCA bins;
e. allowing a predetermined time to lapse thereby allowing electronic output signals to accumulate in said MCA;

f. calculating λ for each electronic signal stored in a particular bin in said MCA memory;

g. correcting for X-ray source spectrum variation;

h. correcting for a change of intensity by distance $R^2$;

i. calculating "d" spacing for a specimen using the equation nλ=2d(sin θ); and j. storing said processed data in a data file in said memory; and k. means to display said data file.

28. A scanning X-ray diffraction system for performing specimen phase analysis having a computer system having a memory, an output, and a central processing unit(CPU) coupled to said memory, said CPU controlling the state of a plurality of processes for controlling the operation of the scanning X-ray diffraction system comprising:

a. an x-ray source;

b. first processor means for sweeping said X-ray source in a predetermined multi-dimensional pattern;

c. second processor means causing said X-ray source to emit X rays successively from different locations in said predetermined pattern relative to a specimen, said second processor means being adjustable by an operator to set a wavelength λ;

d. at least one X-ray detector spaced apart from said x-ray source to receive X rays transmitted to a specimen, said detector having a radiation sensitive region and having means for producing an electrical output signal indicative of X rays impinging on said sensitive region of said detector;

e. an X-ray collimator disposed between a specimen and said detector describing a collimator path;

f. a memory for storing data files;

g. a CPU for receiving said electrical output signal and processing comprising the steps of:

setting a wavelength for said X-ray source;

correlating the position of said X-ray source to said detector electrical output signal;

calculating a distance R between said X-ray source and the centroid of a sensed volume in a specimen;

calculating an angle 2θ between said distance R and a collimator path;

resetting a photon counter to count said electronic output signals;

allowing a predetermined time to lapse to allow on counts to accumulate;

reading said counter;

calculating "d" spacing using the equation nλ=2d(sin θ);

storing said processed data in a data file in said memory; and h. means to output said data file.

29. The system for controlling the operation of the scanning X-ray diffraction system as in claim 28, wherein said first processor means comprises a scanning X-ray source.

30. The system for controlling the operation of the scanning X-ray diffraction system as in claim 29, wherein said second processor means comprises a scanning X-ray source.

31. The system for controlling the operation of the scanning X-ray diffraction system as in claim 30, wherein said means to output comprises an input/output device.

32. The scanning X-ray diffraction system for performing specimen phase analysis having a computer system having a memory, a display device, and a central processing unit (CPU) coupled to said memory, said CPU controlling the state of a plurality of processes for controlling the operation of the scanning X-ray diffraction system as in claim 28 comprising:

a. a multiple channel analyzer(MCA) for processing said electric output signals, said MCA having a memory comprising a plurality of bins for storing said electronic output signals, said electronic output signals representing the wavelength of an X-ray;

b. said MCA connected to said CPU for sending and receiving signals from said MCA;

c. processing of said electronic signals by said CPU to create a data file further comprising the steps of;

d. allowing a predetermined time to lapse thereby allowing photon counts to accumulate in said MCA;

e. calculating λ of an electronic signal stored in a particular bin in said MCA memory;

f. correcting for X-ray source spectrum variation;

g. correcting for a distance $R_p$;

h. calculating "d" spacing for a specimen using the equation nλ=2d(sin θ);

i. storing said processed data in a data file having data points in said memory; and j. means to plot said data points.

33. A scanning X-ray diffraction system for performing specimen analysis resulting in a color Laue pattern having a computer system having a memory, an output, and a central processing unit(CPU) coupled to said memory, said CPU controlling the state of a plurality of processes for controlling the operation of the scanning X-ray diffraction system comprising:

a. an X-ray source;

b. first processor means for sweeping said X-ray source in a predetermined multi-dimensional pattern;

c. second processor means causing said X-ray source to emit X-rays successively from different locations in said predetermined pattern relative to a specimen;

d. at least one x-ray detector spaced apart from said x-ray source to receive x-rays transmitted to a specimen, said detector having a radiation sensitive region and having means for producing an electrical output signal indicative of x-rays impinging on said sensitive region of said detector;

e. an x-ray collimator disposed between a specimen and said detector describing a collimator path;

f. a memory for storing data files;

g. a CPU having an MCA for receiving said electrical output signals and processing comprising the steps of:

inputting the number of pixels in said x-ray source;

inputting the photon count acquisition time, said photon count corresponding to said output signals;

inputting the number of sensed volume slices for a specimen;

commanding the x-ray source to move sequentially in three dimensions, each movement to the location of each of said pixels;

commanding the MCA to accumulate photon counts at each of said pixel locations storing each of said photon counts in a respective MCA memory location;

transferring the pixel location data stored in said MCA memory to a data structure;

using said pixel location data to calculate the coordinates of a centroid of a sensed volume;

calculating the path distance Rp between a centroid and a respective pixel;

calculating an angle 2θ between path distance Rp and a collimator path;

calculating a rotation angle λ;
scaling said spectrum data by factor $Rp^2$;
summing said scaled spectrum data;
storing said scaled spectrum data to a file in memory;
processing each respective pixel;
storing said scaled spectrum data in a file in said memory; and
means to output said scaled spectrum data.

34. A method of obtaining X-ray diffraction measurements using a scanning X-ray diffraction system comprising the steps of:
a. emitting X rays;
b. sweeping said X rays in a predetermined multi-dimensional pattern thereby emitting X rays successively from different positions relative to a specimen and to vary the Bragg angle between X rays transmitted to and diffracted by the specimen;
c. positioning an X-ray detector spaced apart from said X-ray source for receiving X-rays transmitted to and diffracted by a specimen, said X-ray detector producing an electrical output signal indicative of said diffracted X-rays impinging on said detector; and
d. disposing a X-ray collimator between the specimen and said detector, said X-ray collimator placed relatively close to a specimen as compared to a specimen-to-X-ray source distance.

35. The method of obtaining X-ray diffraction measurements using a scanning X-ray diffraction system as in claim 34 further comprising the step of:
a. disposing said collimator adjacent to said detector and in alignment with said detector thereby causing said detector to receive diffracted radiation from the specimen.

36. The method of obtaining X-ray diffraction measurements using an X-ray scanning system as in claim 35 further comprising the steps of:
a. sweeping said X-ray source using a processing means for correlating the position of the X-ray source with an electrical output signal.

37. The method of obtaining X-ray diffraction measurements using an X-ray scanning system as in claim 36 further comprising the step of:
a. counting the signal pulses of said electric output signal.

38. The method of obtaining X-ray diffraction measurements using an X-ray scanning system as in claim 37 further comprising the step of:
a. sorting by wavelength each electric output signal.

39. The method of obtaining X-ray diffraction measurements using an X-ray scanning system as in claim 38 further comprising the steps of:
a. correlating a display with that of said means for sweeping said X-ray source and said display having an intensity control responsive to said processor means.

40. The method of obtaining X-ray diffraction measurements using an X-ray scanning system as in claim 39 wherein said step of sweeping said X-ray source in a multi-dimensional pattern comprises sweeping in a 2-D sweep relative to a specimen.

41. The method of obtaining X-ray diffraction measurements using an X-ray scanning system as in claim 40 wherein said step of sweeping said X-ray source in a multi-dimensional pattern comprises sweeping in a 3-D sweep.

42. The method of obtaining X-ray diffraction measurements using a scanning X-ray diffraction system as in claim 41 further comprising the step of:
a. moving said detector to a plurality of positions on a spherical geometry; and
b. aligning diffracted X-rays with said detector at each position with a collimator;
said spherical geometry having a specimen at its center and said collimator having an axis aligned with a radius from said detector.

43. The method of obtaining X-ray diffraction measurements using a scanning X-ray diffraction system as in claim 42 further comprising the step of:
a. moving said collimator to a plurality of radial positions relative to said detector;
b. aligning diffracted x-rays with the radiation sensitive region of a detector at each position.

44. A scanning X-ray diffraction system for X-ray diffraction measurements comprising:
a. an X-ray source;
b. means for sweeping said X-ray source in a predetermined multi-dimensional pattern to emit X rays successively from different positions relative to a specimen and to vary the Bragg angle between X rays transmitted to and diffracted by the specimen;
c. an X-ray detector spaced apart from said X-ray source to receive said X rays transmitted to and diffracted by the specimen, said X-ray detector having a radiation sensitive region and having means for producing an electrical output signal indicative of said diffracted X rays impinging on said radiation sensitive region of said detector;
d. an X-ray collimator disposed between the specimen and said detector, said X-ray collimator, directing X rays diffracted by the specimen to said X-ray detector; and
e. means for analyzing said electrical output signal from said X-ray detector to determine the wavelength of an X-ray photon producing said electrical output signal.

45. The system of claim 44 in which said means for analyzing said electrical output signal from said X-ray detector comprises a single channel analyzer.

46. The system of claim 44 in which said means for analyzing said electrical output signal from said X-ray detector comprises a multichannel analyzer.

47. The system of claim 44 in which said means for analyzing said electrical output signal from said X-ray detector comprises a single event counter.

48. The system of claim 44 in which said means for analyzing said electrical output signal from said X-ray detector comprises a single rate meter.

* * * * *